US012213809B2

United States Patent
Sakamoto et al.

(10) Patent No.: US 12,213,809 B2
(45) Date of Patent: Feb. 4, 2025

(54) IN-VIVO IMPLANTABLE MEDICAL DEVICE

(71) Applicant: Murata Manufacturing Co., Ltd., Kyoto-fu (JP)

(72) Inventors: Norikazu Sakamoto, Nagaokakyo (JP); Tatsuya Hosotani, Nagaokakyo (JP); Kiyokazu Yamada, Nagaokakyo (JP)

(73) Assignee: Murata Manufacturing Co., Ltd., Kyoto-fu (JP)

( * ) Notice: Subject to any disclaimer, the term of this patent is extended or adjusted under 35 U.S.C. 154(b) by 944 days.

(21) Appl. No.: 17/162,610

(22) Filed: Jan. 29, 2021

(65) Prior Publication Data

US 2021/0152021 A1 May 20, 2021

Related U.S. Application Data

(63) Continuation of application No. PCT/JP2019/016304, filed on Apr. 16, 2019.

(30) Foreign Application Priority Data

Sep. 27, 2018 (JP) .................................. 2018-181758

(51) Int. Cl.
    *A61B 5/00*        (2006.01)
    *A61L 31/02*       (2006.01)
    (Continued)

(52) U.S. Cl.
    CPC ............ *A61B 5/686* (2013.01); *A61B 5/0026* (2013.01); *A61B 5/0031* (2013.01);
    (Continued)

(58) Field of Classification Search
    CPC ............ A61B 5/686; A61B 2560/0219; A61N 1/3787
    See application file for complete search history.

(56) References Cited

U.S. PATENT DOCUMENTS

6,178,353 B1 * 1/2001 Griffith .............. A61N 1/37276
                                                                607/61
2011/0029036 A1   2/2011 Yamamoto et al.
(Continued)

FOREIGN PATENT DOCUMENTS

JP    H107-265442 A   10/1995
JP    2004-352268 A   12/2004
(Continued)

OTHER PUBLICATIONS

Machine translation of JP H07-265442, accessed Nov. 15, 2023.*
(Continued)

*Primary Examiner* — Tammie K Marlen
(74) *Attorney, Agent, or Firm* — Studebaker & Brackett PC

(57) ABSTRACT

An in-vivo implantable medical device includes a housing, an electronic circuit component, a power reception coil, and a magnetic material. The housing is formed of a biocompatible material and forms an internal space. The electronic circuit component is disposed in the internal space. The power reception coil is disposed in the internal space, interacts with an external electromagnetic field to form an electromagnetic resonance field to receive power. At least part of a region of the housing in which the electromagnetic resonance field is formed is formed of a biocompatible nonmetal material.

29 Claims, 15 Drawing Sheets

(51) Int. Cl.
| | |
|---|---|
| *A61L 31/08* | (2006.01) |
| *H01F 27/28* | (2006.01) |
| *H01F 38/14* | (2006.01) |
| *H02J 7/02* | (2016.01) |
| *H02J 50/00* | (2016.01) |
| *H02J 50/12* | (2016.01) |
| *H02J 50/80* | (2016.01) |
| *A61N 1/04* | (2006.01) |
| *A61N 1/05* | (2006.01) |
| *A61N 1/08* | (2006.01) |
| *A61N 1/36* | (2006.01) |
| *H01F 27/24* | (2006.01) |
| *H02J 50/70* | (2016.01) |

(52) U.S. Cl.
CPC ........... *A61L 31/022* (2013.01); *A61L 31/026* (2013.01); *A61L 31/028* (2013.01); *A61L 31/082* (2013.01); *H01F 27/28* (2013.01); *H01F 38/14* (2013.01); *H02J 7/02* (2013.01); *H02J 50/005* (2020.01); *H02J 50/12* (2016.02); *H02J 50/80* (2016.02); *A61B 5/0036* (2018.08); *A61B 2560/02* (2013.01); *A61B 2560/0219* (2013.01); *A61B 2560/0406* (2013.01); *A61L 31/024* (2013.01); *A61L 2400/18* (2013.01); *A61N 1/0472* (2013.01); *A61N 1/05* (2013.01); *A61N 1/0529* (2013.01); *A61N 1/056* (2013.01); *A61N 1/08* (2013.01); *A61N 1/3605* (2013.01); *A61N 1/36062* (2017.08); *H01F 27/24* (2013.01); *H02J 50/70* (2016.02)

(56) References Cited

U.S. PATENT DOCUMENTS

| | | | |
|---|---|---|---|
| 2015/0244178 | A1 | 8/2015 | Tang |
| 2016/0199657 | A1* | 7/2016 | Jiang .................. A61N 1/3787 607/61 |

FOREIGN PATENT DOCUMENTS

| | | |
|---|---|---|
| JP | 2017-164192 A | 9/2017 |
| JP | 2018-501021 A | 1/2018 |

OTHER PUBLICATIONS

International Search Report issued in PCT/JP2019/016304; mailed Jul. 23, 2019.

International Preliminary Report on Patentability and Written Opinion issued in PCT/JP2019/016304; issued Mar. 23, 2021.

An Office Action; "Notice of Reasons for Refusal," mailed by the Japanese Patent Office on Dec. 14, 2021, which corresponds to Japanese Patent Application No. 2020-547937 and is related to U.S. Appl. No. 17/162,610 with English translation.

Tatsuya Hosotani et al.; "MHz-Band Magnetic Coupling Wireless Power Transfer Technology for Small Appliances"; 2016 National Convention of the Institute of Electrical Engineers of Japan; Mar. 16-18, 2016; Vo. 4; total 6 pages; Japan.

* cited by examiner

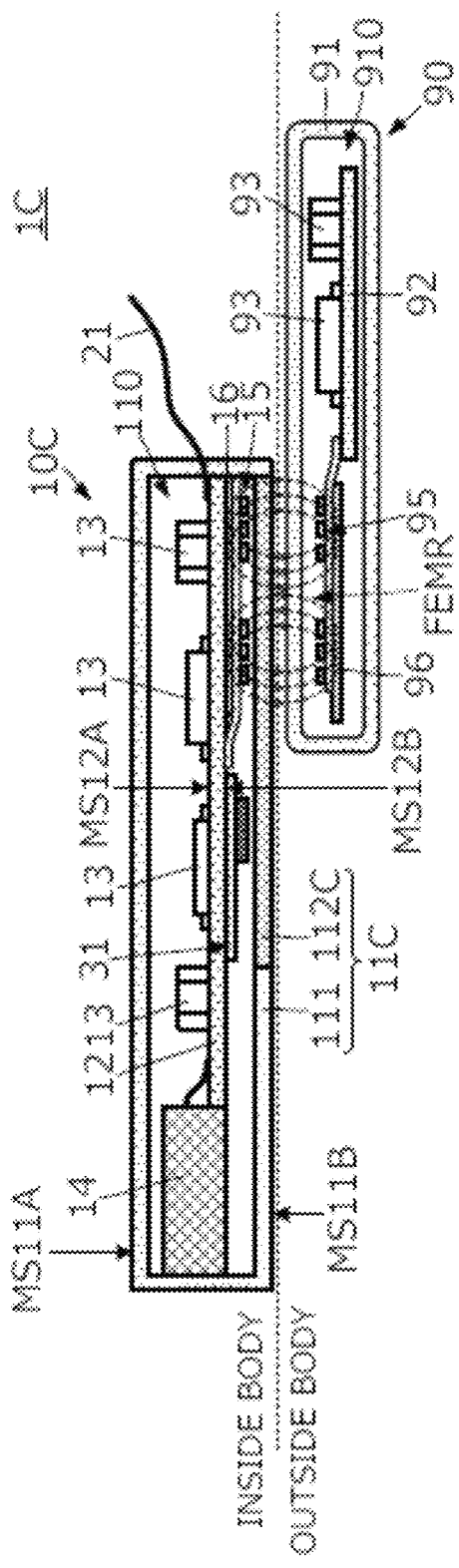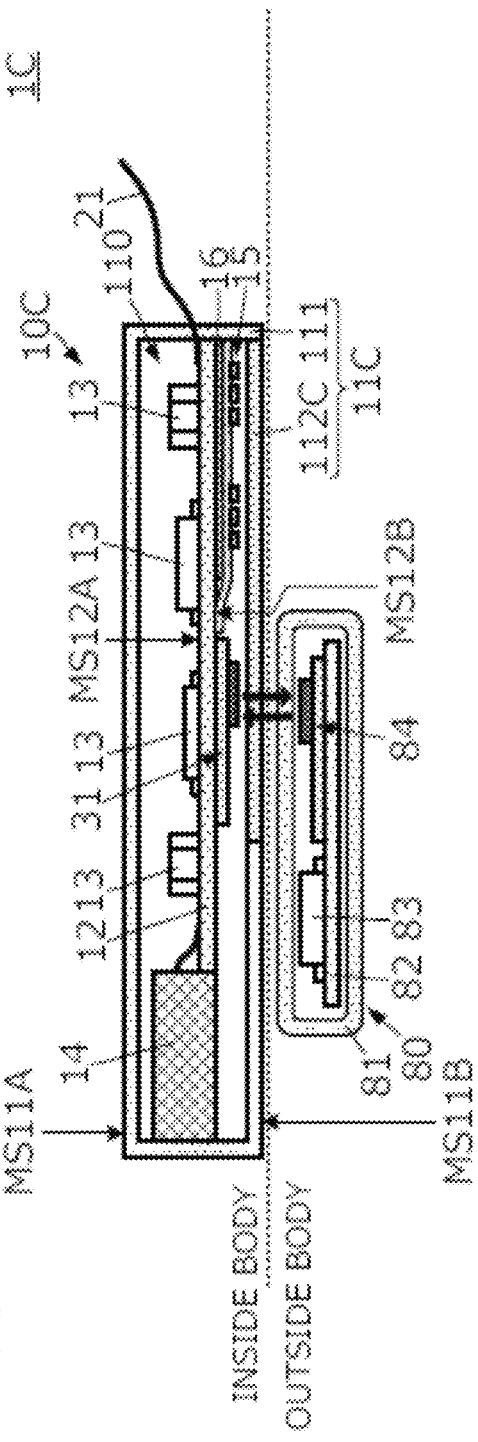

FIG. 13
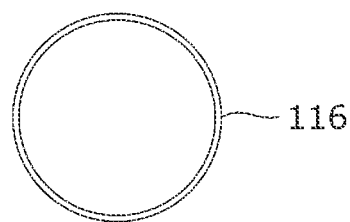
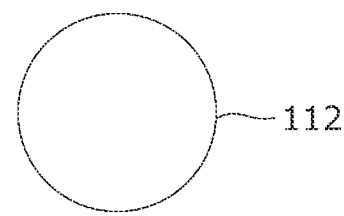
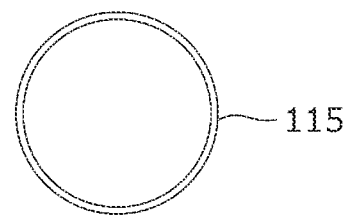
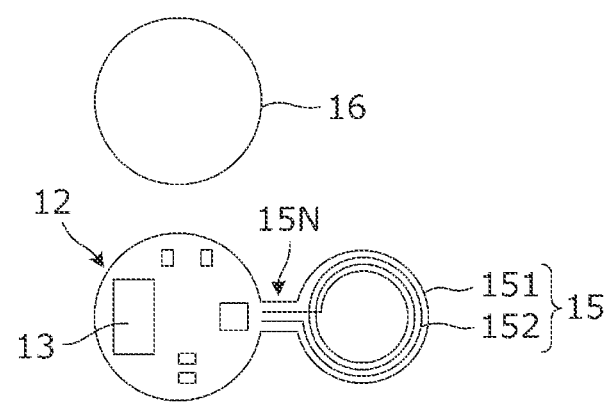
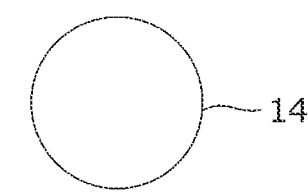
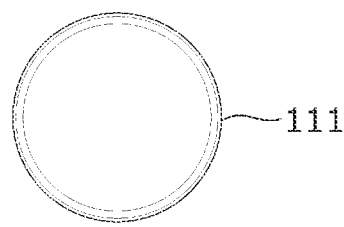

IN-VIVO IMPLANTABLE MEDICAL DEVICE

CROSS-REFERENCE TO RELATED APPLICATIONS

This application claims benefit of priority to International Patent Application No. PCT/JP2019/016304, filed Apr. 16, 2019, and to Japanese Patent Application No. 2018-181758, filed Sep. 27, 2018, the entire contents of each are incorporated herein by reference.

BACKGROUND

Technical Field

The present disclosure relates to an in-vivo implantable medical device that is used by being embedded (implanted) in the body of, for example, a living person or animal, and is wirelessly powered from the outside of the living body.

Background Art

Japanese Unexamined Patent Application Publication No. 2017-164192 describes an in-vivo implantable medical device having a structure in which power is supplied from the outside. The device includes a device main body, a power reception coil, a secondary battery, and an electronic circuit. The power reception coil, the secondary battery, and the electronic circuit are housed inside the device main body.

The power reception coil is realized by a conductor that is helically wound and formed in a tubular shape. The power reception coil and a circuit board on which the electronic circuit is mounted are disposed side by side in plan view of the device main body.

SUMMARY

In the in-vivo implantable medical device described in Japanese Unexamined Patent Application Publication No. 2017-164192, it is not easy to increase a coupling degree in magnetic field coupling between the power reception coil and a power transmission coil, and it is difficult to improve power receiving efficiency. In addition, in general, sapphire, ruby, glass, ceramic, or the like, which is a material excellent in biocompatibility, is difficult to process as a housing. On the other hand, although a biocompatible material made of metal such as titanium is easy to process as a housing, when such a metal housing is used, it is not easy to form magnetic coupling through the housing. In addition, a problem arises in that an eddy current is generated in the metal housing by an external magnetic field, and the housing generates heat.

Accordingly, the present disclosure provides an in-vivo implantable medical device having high power receiving efficiency.

An in-vivo implantable medical device of the present disclosure includes a housing, a power reception coil, a power storage device, and an electronic circuit. The housing is formed of a biocompatible material and forms a sealed space therein. The power reception coil is disposed in the sealed space, interacts with an external electromagnetic field, and forms an electromagnetic resonance field to receive power. The power storage device is disposed in the sealed space and stores the power received through the power reception coil. The electronic circuit is disposed in the sealed space and performs at least signal processing using the power received by the power reception coil or the power stored in the power storage device. At least part of a region of the housing in which the electromagnetic resonance field is formed is formed of a biocompatible nonmetal material.

In addition, an in-vivo implantable medical device of the present disclosure includes a housing, a power reception coil, and an electronic circuit. The housing is formed of a biocompatible material and forms a sealed internal space. The power reception coil is disposed in the internal space. The electronic circuit is disposed in the internal space and performs signal processing with power received by the power reception coil. Then, a region of the housing in which the power reception coil faces an outside of the housing is formed of a biocompatible nonmetal material.

In addition, an in-vivo implantable medical device of the present disclosure includes a housing, a power reception coil, and an electronic circuit. The housing is formed of a biocompatible material and forms a sealed internal space. The power reception coil is disposed in the internal space. The electronic circuit is disposed in the internal space and performs signal processing with power received by the power reception coil. Then, the housing includes a portion made of a biocompatible nonmetal material in a power reception path of power by the power reception coil, and a region of the housing other than a region formed of a biocompatible nonmetal material is formed of a biocompatible metal material.

According to the present disclosure, an in-vivo implantable medical device having high power receiving efficiency is obtained.

BRIEF DESCRIPTION OF THE DRAWINGS

FIG. 8A and FIG. 8B are sectional views illustrating a configuration of a power supply/communication system according to the fourth embodiment of the present disclosure;

FIG. 13 is an exploded plan view of the in-vivo implantable medical device;

DETAILED DESCRIPTION

Figure 1:
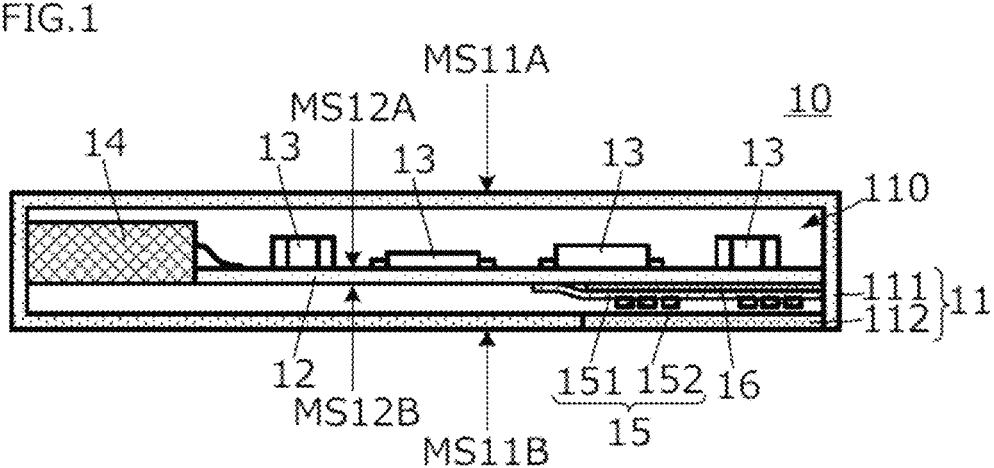
FIG. 1 is a sectional view illustrating a configuration of an in-vivo implantable medical device according to a first embodiment of the present disclosure.

Hereinafter, some specific examples will be illustrated with reference to the drawings, and a plurality of embodiments for implementing the present disclosure will be described. In the drawings, the same reference numerals are given to the same parts. In consideration of ease of description or understanding of main points, for convenience of description, description will be given as a plurality of embodiments, but partial substitutions or combinations of configurations described in different embodiments are possible. In a second and subsequent embodiments, descriptions of matters common to those in a first embodiment will be omitted, and only different points will be described. In particular, similar actions and effects according to similar configurations will not be described in detail for each embodiment.

First Embodiment

Figure 2:
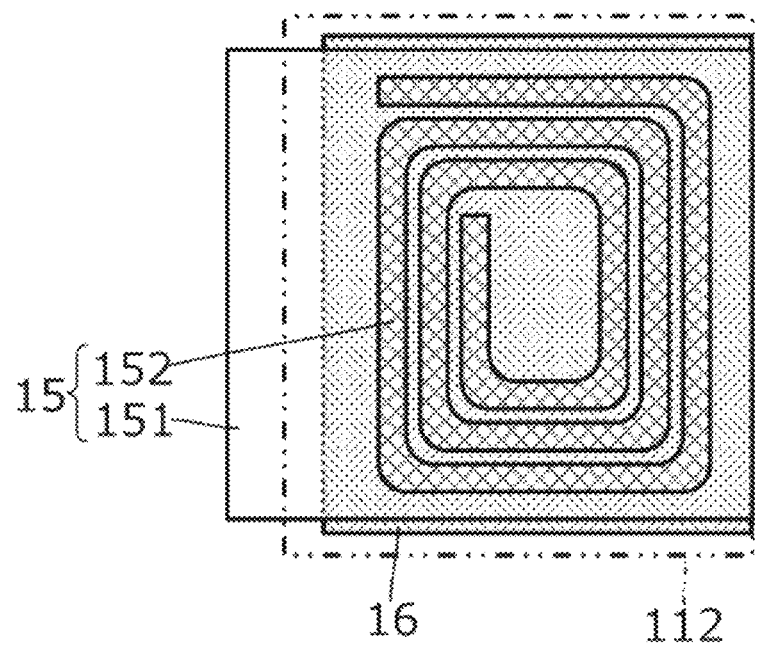
FIG. 2 is a plan view illustrating a positional relationship among a power reception coil, a magnetic material, and a second member made of a biocompatible nonmetal material.

An in-vivo implantable medical device according to a first embodiment of the present disclosure will be described with reference to the drawings. FIG. 1 is a sectional view illustrating a configuration of the in-vivo implantable medical device according to the first embodiment of the present disclosure. FIG. 2 is a plan view illustrating a positional relationship among a power reception coil, a magnetic material, and a second member made of a biocompatible nonmetal material.

As illustrated in FIG. 1, an in-vivo implantable medical device 10 includes the housing 11, a circuit board 12, an electronic circuit component 13, a secondary battery 14, a power reception coil 15, and a magnetic material 16. The secondary battery 14 corresponds to a "power storage device" of the present disclosure.

The housing 11 includes the first member 111 and a second member 112. The housing 11 forms a thin box-like shape by combining the first member 111 and the second member 112 together. The housing 11 has a first main surface MS11A and a second main surface MS11B. The first main surface MS11A and the second main surface MS11B are separated from each other in a height direction of the housing 11, and are each orthogonal to the height direction, and face each other.

The first member 111 has a box-like shape having an opening in part of the second main surface MS11B, and the second member 112 has a flat plate shape. The second member 112 is fitted into the opening of the first member 111.

As described above, the housing 11 has the box-like shape, and thus has an internal space 110. The internal space 110 is a sealed space. Note that, the sealed space in the present application is preferably a space completely shielded from the factors external to the housing 11. However, the circuit board 12, the electronic circuit component 13, the secondary battery 14, the power reception coil 15, and the magnetic material 16 disposed in the internal space 110 may be in a state of being affected by factors external to the housing 11, to an extent that functions as the in-vivo implantable medical device 10 are hardly affected.

The first member 111 is a molded body of a biocompatible metal material. For example, the first member 111 is made of Ti (pure titanium) or a Ti alloy such as Ti-6Al-4V. By using such a material for the first member 111, it is possible to suppress an influence on a living body and an influence from a living body.

As described above, the biocompatible metal material is preferably a material containing Ti as a main component, however, as the biocompatible metal material, a material such as stainless steel containing Cr or Mo, a Co—Cr alloy, or the like may be used. Note that it is preferable that the biocompatible metal material be a material with which durability against an environment, stress, and the like can be obtained, and for example, the biocompatible metal material is more preferably a material having a Young's modulus of 100 GPa or more.

The second member 112 is a molded body of a biocompatible nonmetal material. For example, the second member 112 is made of sapphire, ruby, glass, ceramic, or the like. By using such a biocompatible nonmetal material for the second member 112, it is possible to suppress an influence on a living body and an influence from a living body.

Note that, in view of the durability against the environment, the above-described ceramic is preferably fine ceramics using a material such as sapphire or ruby represented by the chemical formula $Al_2O_3$.

In addition, when focusing on easiness of processing, it is preferable to use glass as a biocompatible nonmetal material. That is, when the durability is regarded as important, the material represented by the chemical formula $Al_2O_3$ is used, and when processability is regarded as important for a shape and the like, glass is used. Similarly, a ceramic may also be preferentially employed as appropriate in accordance with characteristics of the ceramic.

The circuit board 12, the electronic circuit component 13, the secondary battery 14, the power reception coil 15, and the magnetic material 16 are disposed in the internal space 110 of the housing 11. Note that, in the following description, the power reception coil 15 and the magnetic material 16 are described as separate from each other, however, the magnetic material 16 may be configured as part of the power reception coil 15.

The circuit board 12 mainly includes an insulating substrate, and on which a conductor pattern for realizing the functions of the in-vivo implantable medical device 10 is formed. The circuit board 12 is a flat plate, and has a first main surface MS12A and a second main surface MS12B. The circuit board 12 is disposed such that the first main surface MS12A and the second main surface MS12B are substantially parallel to the first main surface MS11A and the second main surface MS11B. In this case, in the circuit board 12, the second main surface MS12B is on a side of the second main surface MS11B of the housing 11, and the first main surface MS12A is on a side of the first main surface MS11A of the housing 11.

A plurality of the electronic circuit components 13 is provided for realizing the function of the in-vivo implantable medical device 10, and includes, for example, various kinds of biological sensors, ICs, passive elements, and the like. That is, the plurality of electronic circuit components 13 is a component of an "electronic circuit" that performs the signal processing of the present disclosure. The plurality of electronic circuit components 13 is mounted on the first main surface MS12A of the circuit board 12, and is connected to the conductor pattern of the circuit board 12. Note that, in plan view, a position where the plurality of electronic circuit components 13 is disposed preferably overlaps at least part of a region defined by an outer shape of the power reception coil 15, and is more preferably included in this region. Accordingly, a planar shape of the housing 11 can be reduced, and the in-vivo implantable medical device 10 can be reduced in size.

The secondary battery 14 is a known chargeable and dischargeable battery. The secondary battery 14 preferably has a thin shape. The secondary battery 14 is connected to the conductor pattern of the circuit board 12. Note that, in FIG. 1, the secondary battery 14 is disposed side by side with respect to the circuit board 12, but may be disposed on the first main surface MS12A of the circuit board 12. Note that, the secondary battery 14 is preferably separated from the power reception coil 15. Accordingly, magnetic flux interlinked with a coil opening of the power reception coil 15 hardly reaches the secondary battery 14, and an eddy current is not generated in an electrode of the secondary battery 14, thereby suppressing generation of heat and a decrease in power receiving efficiency of the power reception coil 15 due to an eddy current.

The power reception coil 15 is a planar coil, and includes a base material 151 and a coil conductor 152. The base material 151 has an insulating property, and is a flat film. The coil conductor 152 is formed of a linear conductor and has a spiral shape formed by a two-dimensional curve. The coil conductor 152 is formed on one main surface of the base material 151.

The power reception coil 15 is disposed on a side of the second main surface MS12B of the circuit board 12. At this time, the power reception coil 15 is disposed such that a surface where the coil conductor 152 is formed and the second main surface MS12B are parallel to each other. The coil conductor 152 of the power reception coil 15 is connected to the conductor pattern of the circuit board 12. Note that, in the present embodiment, the coil conductor 152 includes a single layer, but may include a plurality of layers.

The magnetic material 16 is a flat film shaped magnetic sheet. The magnetic material 16 is disposed between the power reception coil 15 and the second main surface MS12B of the circuit board 12. At this time, the magnetic material 16 is disposed such that a main surface thereof is parallel to the surface where the coil conductor 152 is formed and the second main surface MS12B. It is preferable that the magnetic material 16 be in contact with the power reception coil 15 and the second main surface MS12B.

Here, as illustrated in FIG. 2, in plan view of the in-vivo implantable medical device 10, a region where the coil conductor 152 of the power reception coil 15 is formed overlaps the second member 112. That is, the second member 112 is disposed so as to overlap a power receiving path of power by power reception coil 15. Further, the magnetic material 16 overlaps the region where the coil conductor 152 of the power reception coil 15 is formed.

Figure 3:
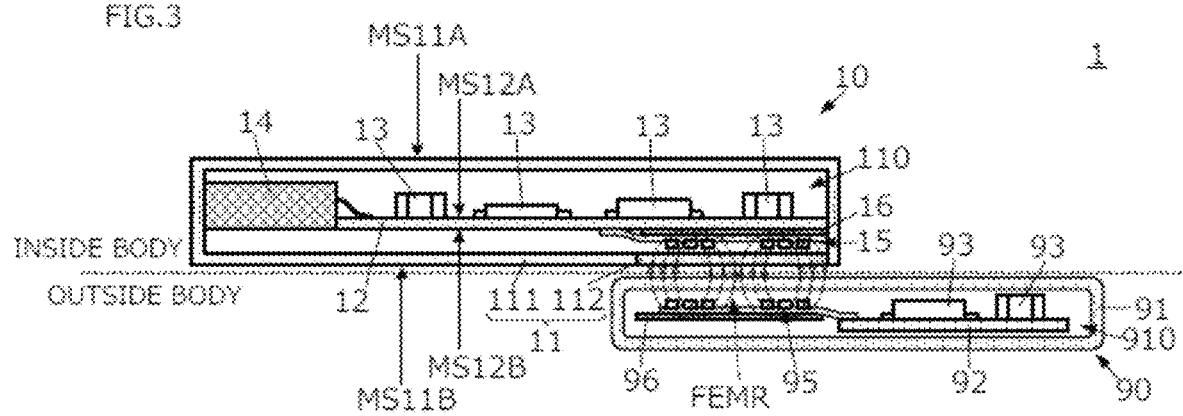
FIG. 3 is a sectional view illustrating a configuration of a power supply system according to the first embodiment of the present disclosure.

The in-vivo implantable medical device 10 having such a configuration is powered by a power supply system as illustrated in FIG. 3. FIG. 3 is a sectional view illustrating a configuration of the power supply system according to the first embodiment of the present disclosure.

As illustrated in FIG. 3, a power supply system 1 includes the in-vivo implantable medical device 10 and the power transmission device 90. The in-vivo implantable medical device 10 is disposed inside a living body, and the power transmission device 90 is disposed outside the living body.

The in-vivo implantable medical device 10 is disposed such that the second main surface MS11B is a side facing a surface of a body (a side facing from the inside of a living body toward the outside of the living body), and the first main surface MS11A is a side facing a center of the inside of the living body.

The power transmission device 90 includes a housing 91, a circuit board 92, an electronic circuit component 93, a power transmission coil 95, and a magnetic material 96.

The housing 91 has a box-like shape and has an internal space 910. The housing 91 is made of a nonmetal material such as resin. The circuit board 92, the electronic circuit component 93, the power transmission coil 95, and the magnetic material 96 are disposed in the internal space 910 of the housing 91.

The circuit board 92 mainly includes an insulating substrate and on which a conductor pattern for realizing a function of the power transmission device 90 is formed.

A plurality of the electronic circuit components 93 is provided for realizing the function of the power transmission device 90, and includes various types of power supply ICs, passive elements, and the like. The plurality of electronic circuit components 93 is mounted on one main surface of the circuit board 92, and is connected to the conductor pattern of the circuit board 92.

The power transmission coil 95 includes a base material and a coil conductor. The base material has an insulating property and is a flat film. The coil conductor is formed of a linear conductor and has a spiral shape formed by a two-dimensional curve. The coil conductor is formed on one main surface of the base material. The power transmission coil 95 is disposed side by side with respect to the circuit board 92. The coil conductor of the power transmission coil 95 is connected to the circuit board 92. Note that, in the present embodiment, the coil conductor of the power transmission coil 95 includes a single layer, but may include a plurality of layers.

The magnetic material 96 is a flat film. The magnetic material 96 is disposed on one main surface side of the power transmission coil 95. Preferably, the magnetic material 96 is in contact with the power transmission coil 95.

The power transmission device 90 is disposed close to the in-vivo implantable medical device 10 such that the power transmission coil 95 has a predetermined positional relationship with the power reception coil 15. At this time, the power transmission device 90 is disposed such that the magnetic material 96 is on a side opposite to the power reception coil 15 with respect to the power transmission coil 95.

For example, specifically, as illustrated in FIG. 3, a region where the power transmission coil 95 is formed and a region where the power reception coil 15 is formed substantially entirely overlap each other in plan view, and are close to each other.

In such a disposition state, between the power reception coil 15 and the power transmission coil 95, the second member 112 made of the biocompatible nonmetal material in the housing 11 of the in-vivo implantable medical device 10, and the housing 91 made of the nonmetal material in the power transmission device 90 are present, and the first member 111 made of the biocompatible metal material in the housing 11 of the in-vivo implantable medical device 10 is not present. In this state, when a current for power supply at a predetermined frequency is caused to flow through the power transmission coil 95, the power reception coil 15 interacts with an electromagnetic field generated by the power transmission coil 95, and forms an electromagnetic resonance field FEMR. That is, this region serves as a coupling region for forming the electromagnetic resonance field FEMR for power supply.

Then, as described above, when the power transmission coil 95 and the power reception coil 15 have a predetermined positional relationship, the electromagnetic resonance field FEMR becomes stronger. In other words, the power transmission device 90 is disposed with respect to the in-vivo implantable medical device 10 such that the power transmission coil 95 and the power reception coil 15 form the electromagnetic resonance field FEMR that is strong.

Thereby, the current for power supply efficiently flows through the power reception coil 15, and power is efficiently supplied to the in-vivo implantable medical device 10. That is, power receiving efficiency is improved by disposing the biocompatible nonmetal material in a region for power receiving in the in-vivo implantable medical device 10. This power is stored in the secondary battery 14, and supplied to the electronic circuit component 13 and the like.

Then, by forming the strong electromagnetic resonance field FEMR as described above, leakage of an electromagnetic field out of the electromagnetic resonance field FEMR is suppressed. Thus, it is possible to effectively suppress adverse effects due to an electromagnetic field for supplying power on the circuit board 12 and the electronic circuit component 13 of the in-vivo implantable medical device 10, and a living body in which the in-vivo implantable medical device 10 is embedded.

In addition, in the in-vivo implantable medical device 10, the magnetic material 16 is disposed on a side opposite to a side of the power transmission coil 95 in the power reception coil 15. Accordingly, an end in a thickness direction of the in-vivo implantable medical device 10 in an electromagnetic field generated by the power reception coil 15 and the power transmission coil 95 is closed by the magnetic material 16, and a strong magnetic path passing through a magnetic coupling region is formed. Thus, a magnetic flux density of magnetic field coupling between the power reception coil 15 and the power transmission coil 95 becomes high, and the power receiving efficiency is further improved.

Further, since the circuit board 12 and the electronic circuit component 13 are disposed on a side opposite to the power reception coil 15 with respect to the magnetic material 16, it is possible to suppress electromagnetic interference with the circuit board 12 and the electronic circuit component 13. This improves reliability of the in-vivo implantable medical device 10. Further, in particular, the electronic circuit component 13 and the secondary battery 14 that do not overlap the magnetic material 16 are surrounded by the first member 111 made of the biocompatible metal material, and thus it is possible to suppress the above-described electromagnetic interference during power supply. This further improves the reliability of the in-vivo implantable medical device 10.

Further, other than a side of the electronic circuit component 13 facing a surface of a living body is covered by the first member 111 made of the biocompatible metal material. Thus, a radiation noise from the electronic circuit component 13 is blocked by the first member 111, and an adverse effect on the external factors, such as the inside of the living body, is mainly suppressed. Further, electromagnetic interference with the electronic circuit component 13 by a peripheral device is blocked by the first member 111, and malfunction of the electronic circuit component 13 and the like are suppressed.

As described above, by using the configuration of the present embodiment, it is possible to realize the in-vivo implantable medical device 10 with high power receiving efficiency and high reliability.

In addition, in the present embodiment, it is possible to configure the in-vivo implantable medical device 10 to have a thin shape by using the power reception coil 15 including the coil conductor 152 having the spiral shape formed in the two-dimensional curve. Further, the power reception coil 15 is disposed on the second main surface MS12B of the circuit board 12, and is overlapped with a mounting region of the electronic circuit component 13 in plan view, thus, a planar area of the configuration can be made smaller than that in a configuration in which a power reception coil and a circuit board are disposed side by side as in the techniques in the past. That is, by using the configuration of the present embodiment, it is possible to realize the in-vivo implantable medical device 10 that is small in thickness and size. In addition, even when the in-vivo implantable medical device 10 is reduced in thickness and size as described above, the power receiving efficiency can be improved, and the reliability can be improved.

Further, since the power reception coil 15 has the structure in which the coil conductor 152 is formed on the film-shaped base material 151, the structure for realizing a desired inductance can be realized by various patterns. Thus, a degree of freedom in design of the power reception coil 15 is improved, and it is easy to apply the power reception coil 15 to the thin and small in-vivo implantable medical device 10.

Note that, the configuration of the present embodiment is suitable for a mode in which the in-vivo implantable medical device 10 autonomously performs predetermined processing (measurement, application of an electric signal, and the like) to a living body. However, by providing the electronic circuit component 13 with a circuit element for wireless communication, data communication using the magnetic coupling between the power transmission coil 95 and the power reception coil 15 can be performed. Accordingly, the in-vivo implantable medical device 10 can obtain a control signal for performing the predetermined processing (measurement, application of an electric signal, and the like) to a living body from the outside.

In addition, in the present embodiment, the mode has been illustrated in which the electronic circuit component 13 is mounted only on the side of the first main surface MS12A of the circuit board 12. However, it is also possible to mount the electronic circuit component 13 in a region on a side of the second main surface MS12B of the circuit board 12, as long as the region is surrounded by the first member 111 constituting the first main surface MS11A and the second main surface MS11B. However, it is preferable to mount the electronic circuit component 13 only on the side of the first main surface MS12A of the circuit board 12.

Second Embodiment

In a second embodiment, an example of an in-vivo implantable medical device including a biological sensor outside a main body of the in-vivo implantable medical device will be illustrated.

Figure 4:
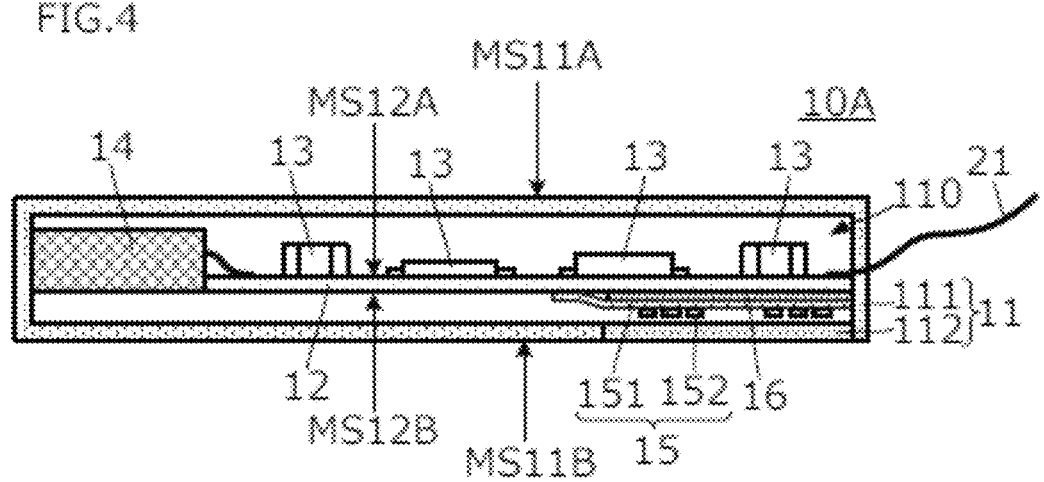
FIG. 4 is a sectional view illustrating a configuration of an in-vivo implantable medical device according to a second embodiment of the present disclosure.

FIG. 4 is a sectional view illustrating a configuration of the in-vivo implantable medical device according to the second embodiment of the present disclosure.

As illustrated in FIG. 4, an in-vivo implantable medical device 10A according to the second embodiment differs from the in-vivo implantable medical device 10 according to the first embodiment in that a biological sensor 21 is added. Other configurations of the in-vivo implantable medical device 10A are similar to those of the in-vivo implantable medical device 10, and description of similar parts will be omitted.

The biological sensor 21 has, for example, a linear shape as illustrated in FIG. 4. One end of the biological sensor 21 in an extending direction is connected to the circuit board 12. The biological sensor 21 is inserted into a hole (not illustrated) formed in the first member 111 of the housing 11. The other end of the biological sensor 21 in the extending direction is disposed outside the housing 11 of the in-vivo implantable medical device 10A, that is, inside a living body. By using the biological sensor 21, the in-vivo implantable medical device 10A can provide a predetermined electric signal or the like to a living body. Further, by using the biological sensor 21 and a further added sensor other than the biological sensor 21, it is possible to obtain a predetermined biological potential with respect to a living body.

Note that, the hole for the biological sensor 21 formed in the first member 111 is filled with a biocompatible nonmetal material. This ensures sealability of the internal space 110 of the housing 11.

Third Embodiment

In a third embodiment, an example of an in-vivo implantable medical device including a built-in communication module that communicates with an external communication module will be illustrated.

Figure 5:
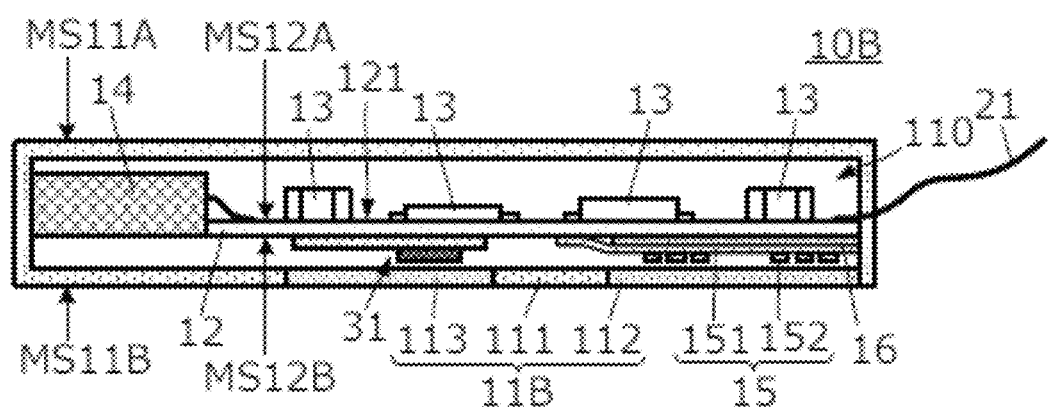
FIG. 5 is a sectional view illustrating a configuration of an in-vivo implantable medical device according to a third embodiment of the present disclosure.

FIG. 5 is a sectional view illustrating a configuration of the in-vivo implantable medical device according to the third embodiment of the present disclosure.

As illustrated in FIG. 5, an in-vivo implantable medical device 10B according to the third embodiment is configured such that the in-vivo implantable medical device 10A according to the second embodiment includes a built-in communication module 31, and a housing 11B of the in-vivo implantable medical device 10B includes a third member 113. Other configurations of the in-vivo implantable medical device 10B are similar to those of the in-vivo implantable medical device 10A, and description of similar parts will be omitted.

A housing 11B includes the first member 111, the second member 112, and the third member 113. Similar to the second member 112, the third member 113 is made of a biocompatible nonmetal material.

The first member 111 has two openings that are separated from each other in the second main surface MS11B. The second member 112 is fitted into one opening of the two openings in the first member 111, and the third member 113 is fitted into the other opening.

The built-in communication module 31 includes a planar communication antenna and a communication IC. These are mounted or formed on a circuit board for the built-in communication module 31. Communication realized by the built-in communication module 31 is data communication. This communication is realized with near field communication, such as MICS in a 400 MHz band, Wi-Fi for a 2.4 GHz band, Bluetooth (registered trademark) for the 2.4 GHz band, Bluetooth Low Energy (registered trademark) for the 2.4 GHz band, Wi-Fi for a 5.0 GHz band, and the like, and power consumption thereof is preferably low.

The built-in communication module 31 is mounted on the second main surface MS12B of the circuit board 12. The built-in communication module 31 is separated from the power reception coil 15, and in plan view, is disposed such that the communication antenna of the built-in communication module 31 overlaps the third member 113.

Figure 6:
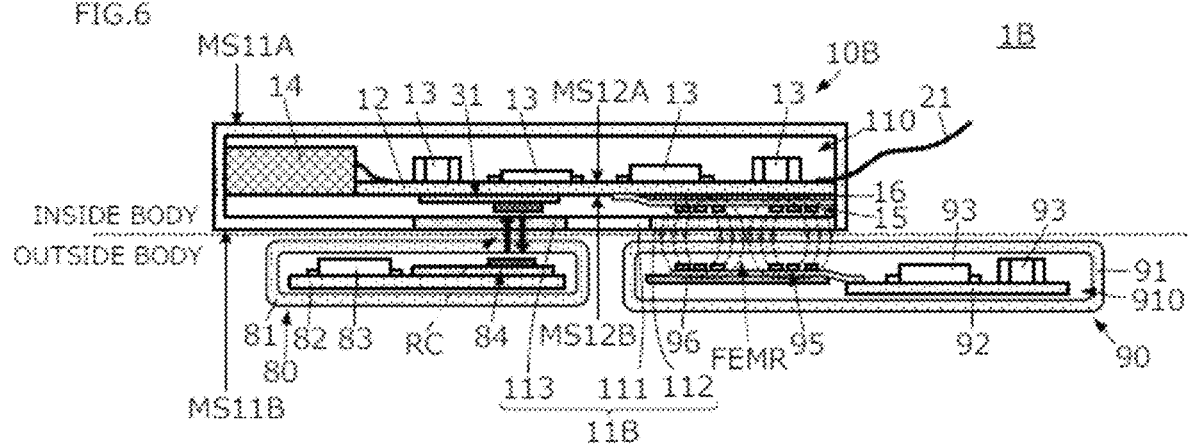
FIG. 6 is a sectional view illustrating a configuration of a power supply/communication system according to the third embodiment of the present disclosure.

The in-vivo implantable medical device 10B having such a configuration is powered and performs data communication by a power supply/communication system as illustrated in FIG. 6. FIG. 6 is a sectional view illustrating a configuration of the power supply/communication system according to the third embodiment of the present disclosure.

As illustrated in FIG. 6, a power supply/communication system 1B includes the in-vivo implantable medical device 10B, the power transmission device 90, and an external communication device 80. The in-vivo implantable medical device 10B is disposed in a living body, and the power transmission device 90 and the external communication device 80 are disposed outside the living body. A configuration of the power transmission device 90 and a disposition mode with respect to the in-vivo implantable medical device 10B are similar to those in the power supply system 1 illustrated in the first embodiment, and description thereof will be omitted.

The external communication device 80 includes a housing 81, a circuit board 82, an electronic circuit component 83, and a communication module 84.

The housing 81 has a box-like shape and has an internal space. The housing 81 is made of a nonmetal material such as resin. The circuit board 82, the electronic circuit component 83, and the communication module 84 are disposed in the internal space of the housing 81. The electronic circuit component 83 and the communication module 84 are mounted on the circuit board 82.

The external communication device 80 is disposed close to the in-vivo implantable medical device 10B such that the third member 113 is interposed and the first member 111 is not interposed, between the communication module 84 and the built-in communication module 31. Thereby, the communication module 84 and the built-in communication module 31 can realize short-range wireless communication.

With this configuration, metal (conductor) is not interposed in a radiation region of a radio wave for data communication, and the in-vivo implantable medical device 10B can obtain a control signal for realizing predetermined processing (measurement, application of an electric signal, and the like) to a living body from the external communication device 80.

Since the built-in communication module 31 and the power reception coil 15 are separated from each other by using the configuration of the in-vivo implantable medical device 10B, mutual interference therebetween can be suppressed even when wireless communication for data communication and power supply are simultaneously performed. Further, the first member 111 made of the biocompatible metal material is disposed between the built-in communication module 31 and the power reception coil 15 in plan view, thus, mutual interference therebetween can be more reliably suppressed, even when wireless communication for data communication and power supply are simultaneously performed.

Fourth Embodiment

In a fourth embodiment, an example of an in-vivo implantable medical device that individually performs power supply and data communication will be illustrated.

Figure 7:
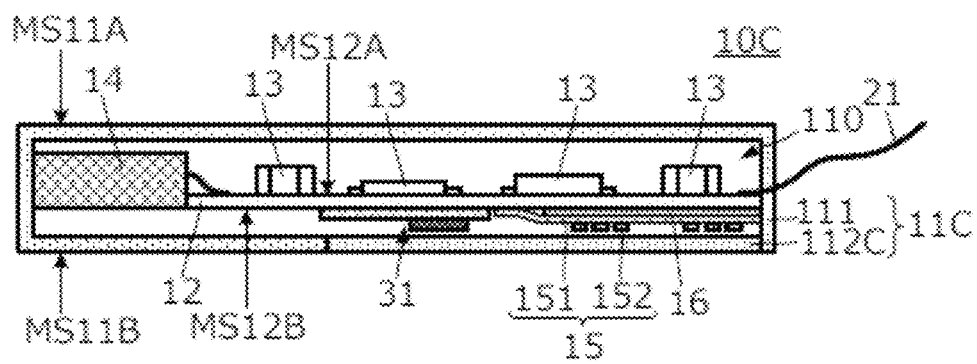
FIG. 7 is a sectional view illustrating a configuration of an in-vivo implantable medical device according to a fourth embodiment of the present disclosure.

FIG. 7 is a sectional view illustrating a configuration of the in-vivo implantable medical device according to the fourth embodiment of the present disclosure.

As illustrated in FIG. 7, an in-vivo implantable medical device 10C according to the fourth embodiment differs from the in-vivo implantable medical device 10B according to the third embodiment, in a positional relationship between the power reception coil 15 and the built-in communication module 31, and accordingly, in a configuration of a housing 11C. Other configurations of the in-vivo implantable medical device 10C are similar to those of the in-vivo implantable medical device 10B, and description of similar parts will be omitted.

The housing 11C includes the first member 111 and a second member 112C. Similar to the second member 112, the second member 112C is made of a biocompatible nonmetal material.

The built-in communication module 31 is disposed so as to be close to the power reception coil 15. The region where the coil conductor 152 in the power reception coil 15 is formed and the built-in communication module 31 overlap the second member 112C in plan view.

The in-vivo implantable medical device 10C having such a configuration is powered and performs data communication by a power supply/communication system as illustrated in FIG. 8A and FIG. 8B. FIG. 8A and FIG. 8B are sectional views illustrating a configuration of a power supply/communication system according to the fourth embodiment of the present disclosure. FIG. 8A illustrates a state during power supply, and FIG. 8B illustrates a state during data communication.

As illustrated in FIG. 8A and FIG. 8B, a power supply/communication system 1C according to the fourth embodiment differs from the power supply/communication system 1B according to the third embodiment, in a configuration of the above-described in-vivo implantable medical device 10C, and differs in that power supply and data communication are individually performed. Other configurations of the power supply/communication system 1C are similar to those of the power supply/communication system 1B, and a description of similar parts will be omitted.

As illustrated in FIG. 8A, during power supply, the power transmission device 90 is brought close to the in-vivo implantable medical device 10C. At this time, as illustrated in the first embodiment, the power transmission device 90 is disposed at a predetermined position with respect to the in-vivo implantable medical device 10C such that the power transmission coil 95 and the power reception coil 15 form an electromagnetic resonance field. In this case, the external communication device 80 is not brought close to the in-vivo implantable medical device 10C. Alternatively, the external communication device 80 does not perform data communication even when the external communication device 80 is brought close to the in-vivo implantable medical device 10C.

As illustrated in FIG. 8B, during data communication, the external communication device 80 is brought close to the in-vivo implantable medical device 10C. In this case, as also illustrated in the third embodiment, the external communication device 80 is disposed with respect to the in-vivo implantable medical device 10C such that the communication module 84 and the built-in communication module 31 are brought close to each other. In this case, the power transmission device 90 is not brought close to the in-vivo implantable medical device 10C. Alternatively, the power transmission device 90 does not perform power supply even when the power transmission device 90 is brought close to the in-vivo implantable medical device 10C.

With such a configuration and processing, mutual interference between wireless communication for data communication and power supply can be reliably suppressed.

Fifth Embodiment

In a fifth embodiment, an example of an in-vivo implantable medical device including a biological sensor outside a housing will be illustrated.

Figure 9:
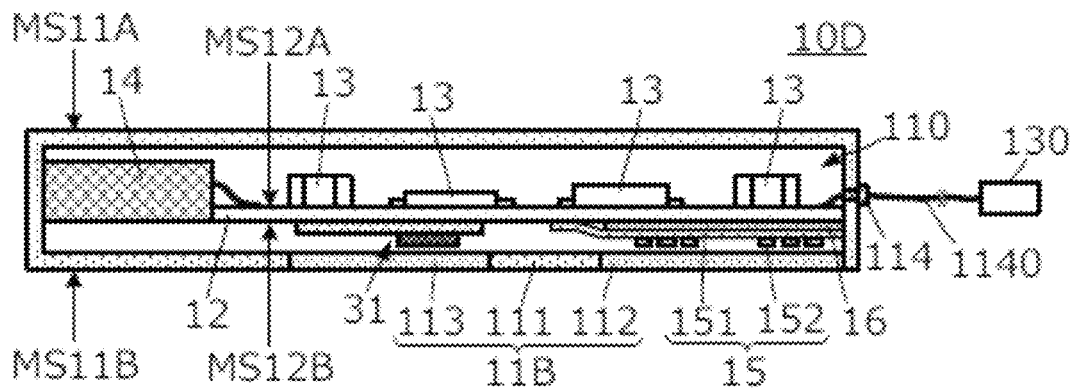
FIG. 9 is a sectional view illustrating a configuration of an in-vivo implantable medical device according to a fifth embodiment of the present disclosure.

FIG. 9 is a sectional view illustrating a configuration of an in-vivo implantable medical device according to the fifth embodiment of the present disclosure.

As illustrated in FIG. 9, an in-vivo implantable medical device 10D according to the fifth embodiment differs from the in-vivo implantable medical device 10 according to the first embodiment in that an external biological sensor 130 is added. There is also a difference in that the built-in communication module 31 is provided, and the third member 113 is provided in the housing 11B. Other configurations of the in-vivo implantable medical device 10D are similar to those of the in-vivo implantable medical device 10, and description of similar parts will be omitted.

The in-vivo implantable medical device 10D includes the biological sensor 130. In addition, the in-vivo implantable medical device 10D includes a feedthrough 114 in a region of the first member 111 in the housing 11B. The feedthrough 114 is disposed at the housing 11B on a side of the first main surface MS12A of the circuit board 12. The biological sensor 130 is connected to the circuit board 12 in the housing 11B through the feedthrough 114 and a cable 1140.

With such a configuration, the biological sensor 130 can be disposed outside the housing 11B, and a degree of freedom in disposition of the biological sensor 130 is improved. At this time, since the feedthrough 114 is disposed on a side of the first main surface MS12A of the circuit board 12, formation of an electromagnetic resonance field is not inhibited.

Sixth Embodiment

In a sixth embodiment, an example of an in-vivo implantable medical device including a solenoid type power reception coil will be illustrated.

Figure 10:
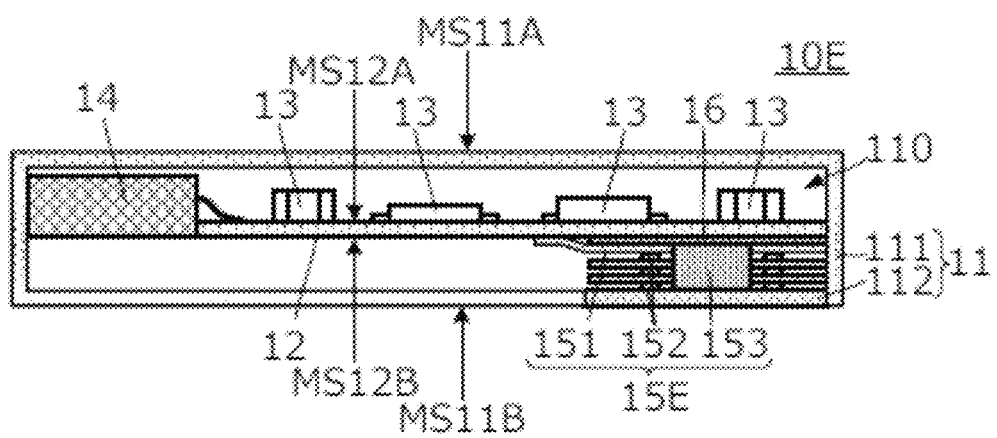
FIG. 10 is a sectional view illustrating a configuration of an in-vivo implantable medical device according to a sixth embodiment of the present disclosure.

FIG. 10 is a sectional view illustrating a configuration of an in-vivo implantable medical device according to the sixth embodiment of the present disclosure.

As illustrated in FIG. 10, an in-vivo implantable medical device 10E according to the sixth embodiment differs from the in-vivo implantable medical device 10 according to the first embodiment in that a solenoid type power reception coil 15E is included. Other configurations of the in-vivo implantable medical device 10E are similar to those of the in-vivo implantable medical device 10, and description of similar parts will be omitted.

The power reception coil 15E is provided with coil conductors 152 including a plurality of stacked layers. The coil conductors 152 including the plurality of layers are sequentially connected in a stacking direction, and form a helical coil. A core material 153 being a magnetic substance is disposed in a central region of the helical coil. According to this configuration, the power reception coil 15E realizes a solenoid type coil.

In such a configuration, it is possible to further concentrate magnetic flux in a center of the power reception coil 15E, and to strengthen an electromagnetic resonance field.

Figure 11A:
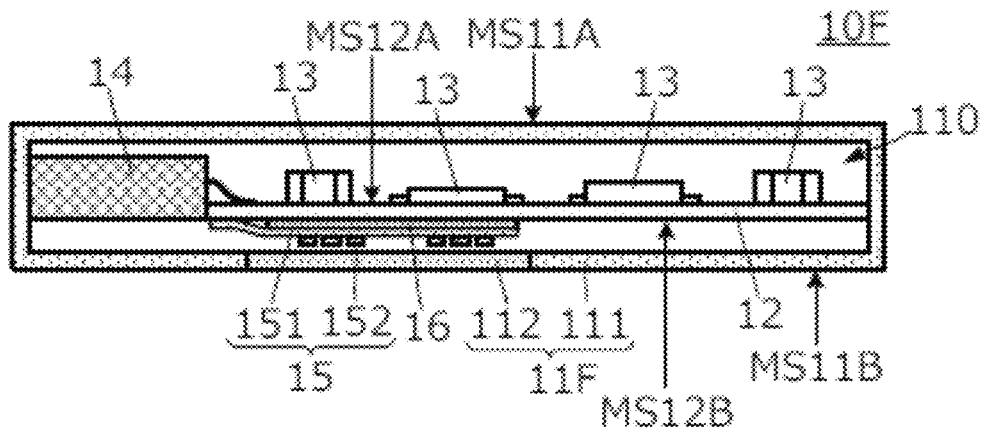
FIG. 11A and FIG. 11B are sectional views each illustrating a derivative example of a configuration of the in-vivo implantable medical device.
Figure 11B:
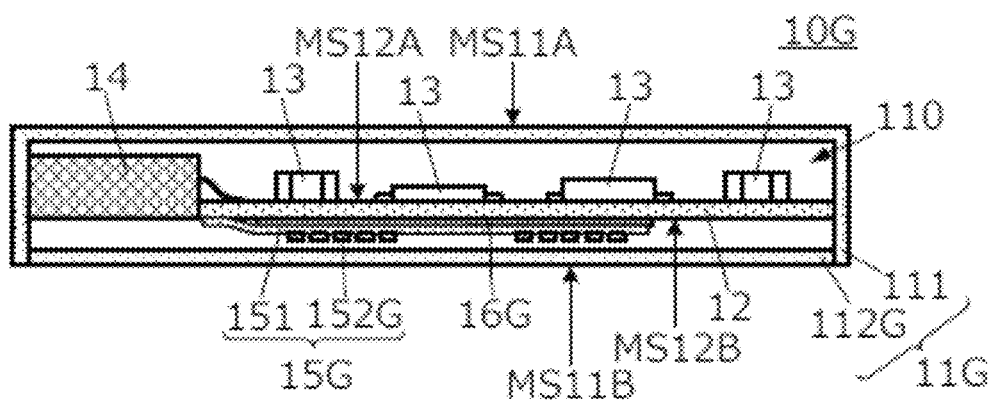

Note that, respective disposition positions and shapes of the power reception coil 15E, the magnetic material 16, and the second member 112 are not limited to those in the configuration described in the above-described embodiment. For example, configurations illustrated in FIG. 11A, FIG. 11B, and the like may be employed. FIG. 11A and FIG. 11B are sectional views each illustrating a derivative example of a configuration of the in-vivo implantable medical device. Note that, FIG. 11A and FIG. 11B each illustrate the derivative example of the in-vivo implantable medical device 10 according to the first embodiment, but a concept of the configuration illustrated in each of FIG. 11A and FIG. 11B can be appropriately applied to an in-vivo implantable medical device according to another embodiment. Hereinafter, only differences from the in-vivo implantable medical device 10 according to the first embodiment will be described.

As illustrated in FIG. 11A, in an in-vivo implantable medical device 10F, the power reception coil 15 and the magnetic material 16 are disposed at a position at an end of the circuit board 12 on a side of the secondary battery 14. Accordingly, the second member 112 is disposed on the second main surface MS11B of a housing 11F at a position close to the secondary battery 14. Then, the power reception coil 15, the magnetic material 16, and the second member 112 overlap each other in plan view.

As illustrated in FIG. 11B, the power reception coil 15E of an in-vivo implantable medical device 10G is larger than the power reception coil 15 according to the first embodiment, and has an area that occupies more than half an area of the second main surface MS12B of the circuit board 12. Accordingly, a coil conductor 152G of a power reception coil 15G has a larger number of turns than that of the coil conductor 152 of the power reception coil 15. Further, with this structure, the coil conductor 152G can have a wider central opening than that of the coil conductor 152.

A magnetic material 16G is disposed so as to overlap a region where the coil conductor 152G is formed.

A housing 11G includes the first member 111 and a second member 112G. The first member 111 has a box-like shape in which one surface (a surface on a side of the second main surface MS11B of the housing 11G) is open. The second member 112G is a flat plate that closes the opening in the first member 111. That is, the entire second main surface MS11B of the housing 11G is formed by the second member 112G.

Even in these configurations, similar operations and advantages to those of the in-vivo implantable medical device 10 according to the first embodiment can be obtained. However, it is preferable that the second member be disposed only in a region in which an electromagnetic resonance field is formed.

Seventh Embodiment

In a seventh embodiment, an in-vivo implantable medical device having a housing excellent in sealability will be illustrated.

Figure 12:
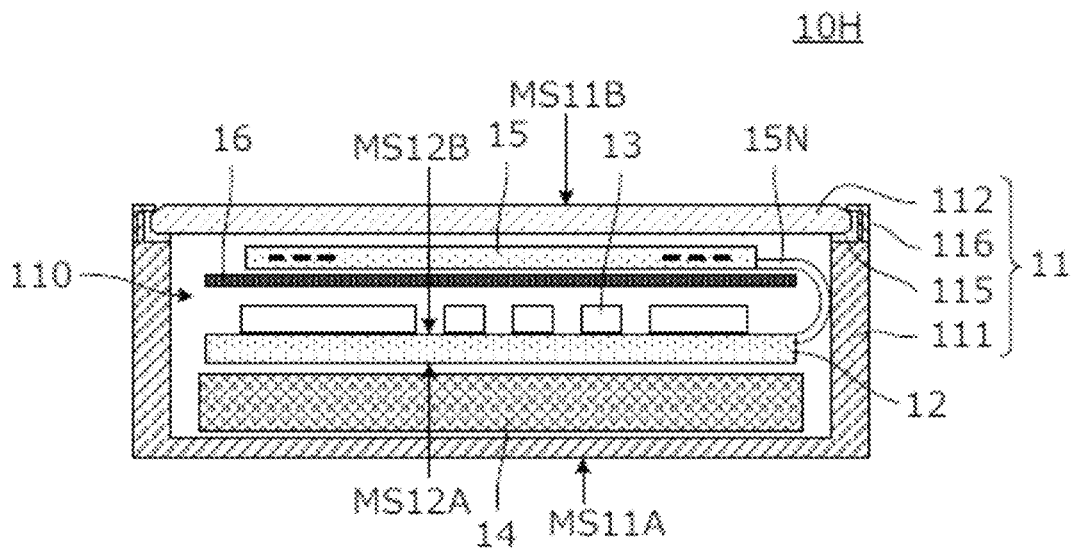
FIG. 12 is a sectional view of an in-vivo implantable medical device according to a seventh embodiment.

FIG. 12 is a sectional view of the in-vivo implantable medical device 10H according to the seventh embodiment. FIG. 13 is an exploded plan view of the in-vivo implantable medical device 10H.

The in-vivo implantable medical device 10H includes the housing 11, the circuit board 12, the electronic circuit component 13, the secondary battery 14, the power reception coil 15, and the magnetic material 16. The secondary battery 14 corresponds to a "power storage device" of the present disclosure.

The housing 11 is constituted by the first member 111, the second member 112, the fixing ring 116, and the packing 115. The fixing ring 116 is an example of a "fixing member" according to the present disclosure. The first member 111 is constituted by a disk-shaped bottom plate portion and a cylindrical side wall portion. The second member 112 has a disk-like shape. The second member 112 is fitted into an opening of the first member 111 with the packing 115 interposed therebetween. Detailed structure of a fitting portion of the second member 112 fit into the first member 111 will be described later. As described above, the housing 11 has a thin cylindrical can shape having the internal space 110 formed by combining the first member 111 and the second member 112 with each other with the packing 115 interposed therebetween. In the present embodiment, a lower surface of the first member 111 is referred to as the first main surface MS11A of the housing 11, and an upper surface (outer surface) of the second member 112 is referred to as the second main surface MS11B of the housing 11.

The first member 111 is a molded body of a biocompatible metal material. For example, the first member 111 is made of Ti (pure titanium) or a Ti alloy such as Ti-6Al-4V. Alternatively, the first member 111 is a sintered material of mixture of ceramic powder and powder of the above titanium alloy. By using such a biocompatible metal material for the first member 111, it is possible to suppress an influence on a living body and an influence from a living body.

As described above, the biocompatible metal material is preferably a material containing Ti as a main component, however, as the biocompatible metal material, a material such as stainless steel containing Cr or Mo, a Co—Cr alloy, or the like may be used. Note that, it is preferable that the biocompatible metal material be a material having durability against an environment, stress, and the like, and for example, the biocompatible metal material is more preferably a material having a Young's modulus of 100 GPa or more.

The second member 112 is a molded body of a biocompatible nonmetal material. For example, the second member 112 is made of sapphire, ruby, glass, ceramic, or the like. By using such a biocompatible nonmetal material for the second member 112, it is possible to suppress an influence on a living body and an influence from a living body.

Note that, in view of the durability against the environment, the above-described ceramic is preferably fine ceramics using a material such as sapphire or ruby represented by the chemical formula $Al_2O_3$.

In addition, when attention is focused on easiness in processing, it is preferable to use glass as a biocompatible nonmetal material.

The packing 115 is a material having more flexibility than the first member 111 and the second member 112, and is a molded body of a synthetic polymer compound having a main skeleton by a siloxane bond, such as silicone rubber. For example, a silicone oil or the like is applied, as a biocompatible oil, to the packing 115.

The circuit board 12, the electronic circuit component 13, the secondary battery 14, the power reception coil 15, and the magnetic material 16 are disposed in the internal space 110 of the housing 11. Note that, in the following description, the power reception coil 15 and the magnetic material 16 are described as being separate from each other, however, the magnetic material 16 may be configured as part of the power reception coil 15.

The circuit board 12 is constituted by an insulating base body on which a predetermined conductor pattern is formed, and the electronic circuit component 13 mounted on the insulating base body. This circuit board 12 includes a main circuit for realizing a function of the in-vivo implantable medical device 10H.

The circuit board 12 is a flat plate and has the first main surface MS12A and the second main surface MS12B. The circuit board 12 is disposed such that the first main surface MS12A and the second main surface MS12B are substantially parallel to the first main surface MS11A and the second main surface MS11B of the housing 11. In addition, the second main surface MS12B of the circuit board 12 is on a side of the second main surface MS11B of the housing 11, and the first main surface MS12A of the circuit board 12 is on a side of the first main surface MS11A of the housing 11.

A plurality of the electronic circuit components 13 is provided for realizing the function of the in-vivo implantable medical device 10H, and includes, for example, various kinds of biological sensors, ICs, passive elements, and the like. That is, the plurality of electronic circuit components 13 is a component of an "electronic circuit" that performs the signal processing of the present disclosure. The plurality of electronic circuit components 13 is mounted on the second main surface MS12B of the circuit board 12, and is connected to a conductor pattern of the circuit board 12.

Note that, in plan view of the second main surface MS12B of the circuit board 12, a position where the plurality of electronic circuit components 13 is disposed preferably overlaps at least part of a region of the power reception coil 15 defined by an outer shape of the power reception coil 15, and it is more preferable that all the electronic circuit components 13 be within the above-described region. This makes it possible to reduce a planar shape of the first main surface MS11A or the second main surface MS11B of the housing 11 and to reduce the size of the in-vivo implantable medical device 10H.

The secondary battery 14 is a known chargeable and dischargeable battery, and is disposed along the first main surface MS12A of the circuit board 12. The secondary battery 14 preferably has a thin shape. The secondary battery 14 is connected to the conductor pattern of the circuit board 12.

As illustrated in FIG. 13, the power reception coil 15 and the circuit board 12 are integrally formed as a single multilayer substrate. The power reception coil 15 is a planar coil, and is constituted by the base material 151 that has an insulating property and the coil conductor 152. The power reception coil 15 is connected to the circuit board 12 with a base portion 15N thereof interposed therebetween. The coil conductor 152 of the power reception coil 15 is connected to the conductor pattern of the circuit board 12. The base portion 15N of the power reception coil has the number of layers of base materials smaller than the number of layers of a portion of the power reception coils 15 and the number of layers of a portion of the circuit board 12, and has flexibility.

The coil conductor 152 is a conductor pattern in which a main portion is formed in a spiral shape of one layer. Note that, the coil conductor 152 may be formed in a plurality of layers.

As illustrated in FIG. 12, the power reception coil 15 is disposed on a side of the second main surface MS12B of the circuit board 12. The power reception coil 15 is disposed such that a surface where the coil conductor 152 is formed and the second main surface MS11B of the housing 11 are parallel to each other.

The magnetic material 16 is a disk-shaped magnetic sheet. The magnetic material 16 is disposed between the power reception coil 15 and the second main surface MS12B of the circuit board 12. The magnetic material 16 is disposed such that a main surface thereof is parallel to a surface where the coil conductor 152 is formed. It is preferable that the magnetic material 16 be in contact with the power reception coil 15.

Since the power reception coil 15 is separated from the secondary battery 14, and the magnetic material 16 is disposed between the power reception coil 15 and the secondary battery 14, substantially no magnetic flux interlinked with a coil opening of the power reception coil 15 reaches the secondary battery, and substantially no eddy current is generated in an electrode of the secondary battery 14, thereby suppressing generation of heat and a decrease in power receiving efficiency of the power reception coil 15 due to an eddy current.

Figure 14:
FIG. 14 is a cutaway perspective view that illustrates a shape of a packing.
Figure 15A:
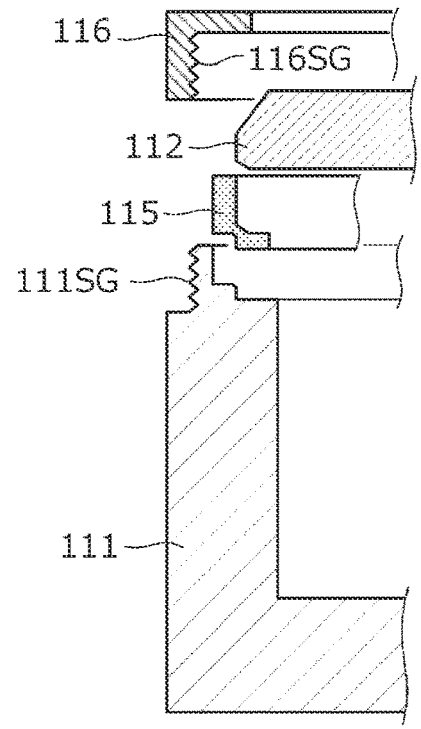
FIG. 15A and FIG. 15B are partial sectional views illustrating structure of a fitting portion of a second member and the like fit into an opening of a first member of a housing.
Figure 15B:
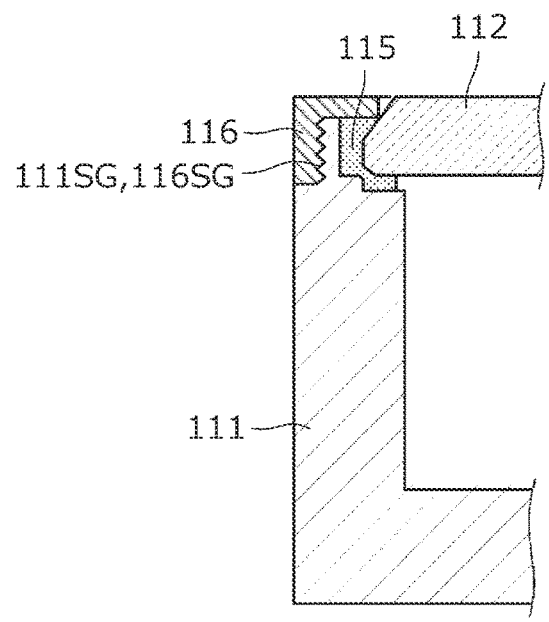

FIG. 14 is a cutaway perspective view illustrating a shape of the above packing 115. FIG. 15A and FIG. 15B are partial sectional views illustrating structure of a fitting portion of the second member and the like fit into an opening of the first member 111 of the housing 11. FIG. 15A is the partial sectional view in a state before the first member 111 and the second member 112 of the housing 11, the fixing ring 116, and the packing 115 are combined with each other. FIG. 15B is the partial sectional view in a state in which the parts are combined with each other.

As illustrated in FIG. 13, FIG. 15A, and FIG. 15B, the fixing ring 116 in an annular shape is provided and holds the second member 112 in a direction in which the second member 112 is fitted into the opening of the first member 111. A screw groove 111SG is formed in an outer peripheral edge of the opening of the first member 111. That is, an external thread is formed in the opening of the first member 111.

An outline of the fixing ring 116 is an annular shape, and a cross-section in a radial direction from a center of the annular shape is an L-shape. A screw groove 116SG is formed in an inner peripheral edge of this fixing ring 116. That is, an internal thread is formed in the fixing ring 116. This screw groove 116SG of the fixing ring 116 is screwed to the screw groove 111SG of the first member 111.

In the state illustrated in FIG. 15A, the packing 115 is attached to an inner peripheral edge of the opening of the first member 111, the second member 112 is placed thereon, and the fixing ring 116 is put thereon further from above, and the screw groove 111SG of the first member 111 is screwed into the screw groove 116SG of the fixing ring 116. Thereby, the second member 112 is pressed toward the first member 111, and the packing 115 is pressed between the first member 111 and the second member 112. The packing 115 is more flexible than the first member 111 and the second member 112, and thus is deformed, and is in close contact with an outer peripheral edge of the second member 112 while being in close contact with the first member 111. Thereby, the structure illustrated in FIG. 15B is obtained.

The fixing ring 116 is made of a biocompatible metal material. For example, similarly to the first member 111, the fixing ring 116 is made of Ti or a Ti alloy such as Ti-6Al-4V.

The packing 115 is made of a biocompatible nonmetal material. For example, silicone rubber for medical applications that does not include organic plasticizers is used, and liquid silicone rubber (LSR) and high-temperature vulcanized silicone rubber (HCR, HTV) are used.

Figure 16:
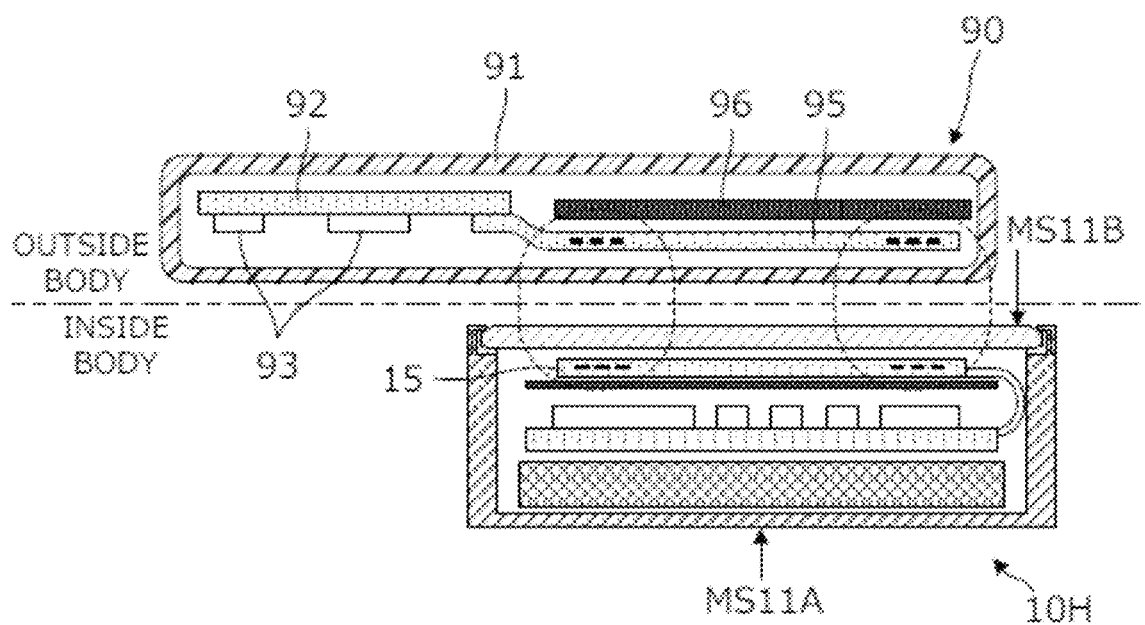
FIG. 16 is a sectional view illustrating a configuration of a power transmission device that supplies power to the in-vivo implantable medical device.

FIG. 16 is a sectional view illustrating a configuration of a power transmission device that supplies power to the in-vivo implantable medical device 10H. FIG. 16 is a sectional view illustrating a state in which the power transmission device is brought close to the in-vivo implantable medical device 10H.

The in-vivo implantable medical device 10H illustrated in FIG. 16 is disposed in a living body, and the power transmission device 90 is disposed outside the living body.

The in-vivo implantable medical device 10H is disposed such that the second main surface MS11B is a side facing a surface of a body (a side facing from the inside of a living body toward the outside of the living body), and the first main surface MS11A is a side facing the inside of the living body.

The power transmission device 90 includes the housing 91, the circuit board 92, the electronic circuit component 93, the power transmission coil 95, and the magnetic material 96.

The housing 91 has a box-like shape. The housing 91 is made of a nonmetal material such as resin. The circuit board 92, the electronic circuit component 93, the power transmission coil 95, and the magnetic material 96 are disposed in an internal space of the housing 91.

A circuit for realizing a function of the power transmission device 90 is included in the circuit board 92.

A plurality of the electronic circuit components 93 is provided for realizing the function of the power transmission device 90, and includes various types of power supply ICs, passive elements, and the like. The plurality of electronic circuit components 93 is mounted on one main surface of the circuit board 92, and is connected to a conductor pattern of the circuit board 92.

The power transmission coil 95 includes a base material and a coil conductor. The base material is a thin plate having an insulating property. Further, the coil conductor is a conductor pattern formed in a spiral shape. The coil conductor is formed on one main surface of the base material. The power transmission coil 95 is disposed side by side with respect to the circuit board 92. A coil conductor of the power transmission coil 95 is connected to the circuit board 92. Note that, in the present embodiment, the coil conductor of the power transmission coil 95 includes a single layer, but may include a plurality of layers.

The magnetic material 96 is a disk-shaped magnetic sheet. The magnetic material 96 is disposed on one main surface side of the power transmission coil 95. Preferably, the magnetic material 96 is in contact with the power transmission coil 95.

The power transmission device 90 is disposed close to the in-vivo implantable medical device 10H such that the power transmission coil 95 has a predetermined positional relationship with the power reception coil 15. At this time, the power transmission device 90 is disposed such that the magnetic material 96 is located on a side opposite to the power reception coil 15 with respect to the power transmission coil 95.

In such a state, the power reception coil 15 and the power transmission coil 95 disposed are magnetically coupled to each other, and power is supplied from the power transmission device 90 to the in-vivo implantable medical device 10H. This power is stored in the secondary battery 14 and supplied to the electronic circuit component 13 and the like.

In the example illustrated in FIG. 16, a region where the coil conductor of the power transmission coil 95 is formed and a region where a coil conductor of the power reception coil 15 is formed substantially entirely overlap each other in plan view, and are close to each other.

Figure 17:
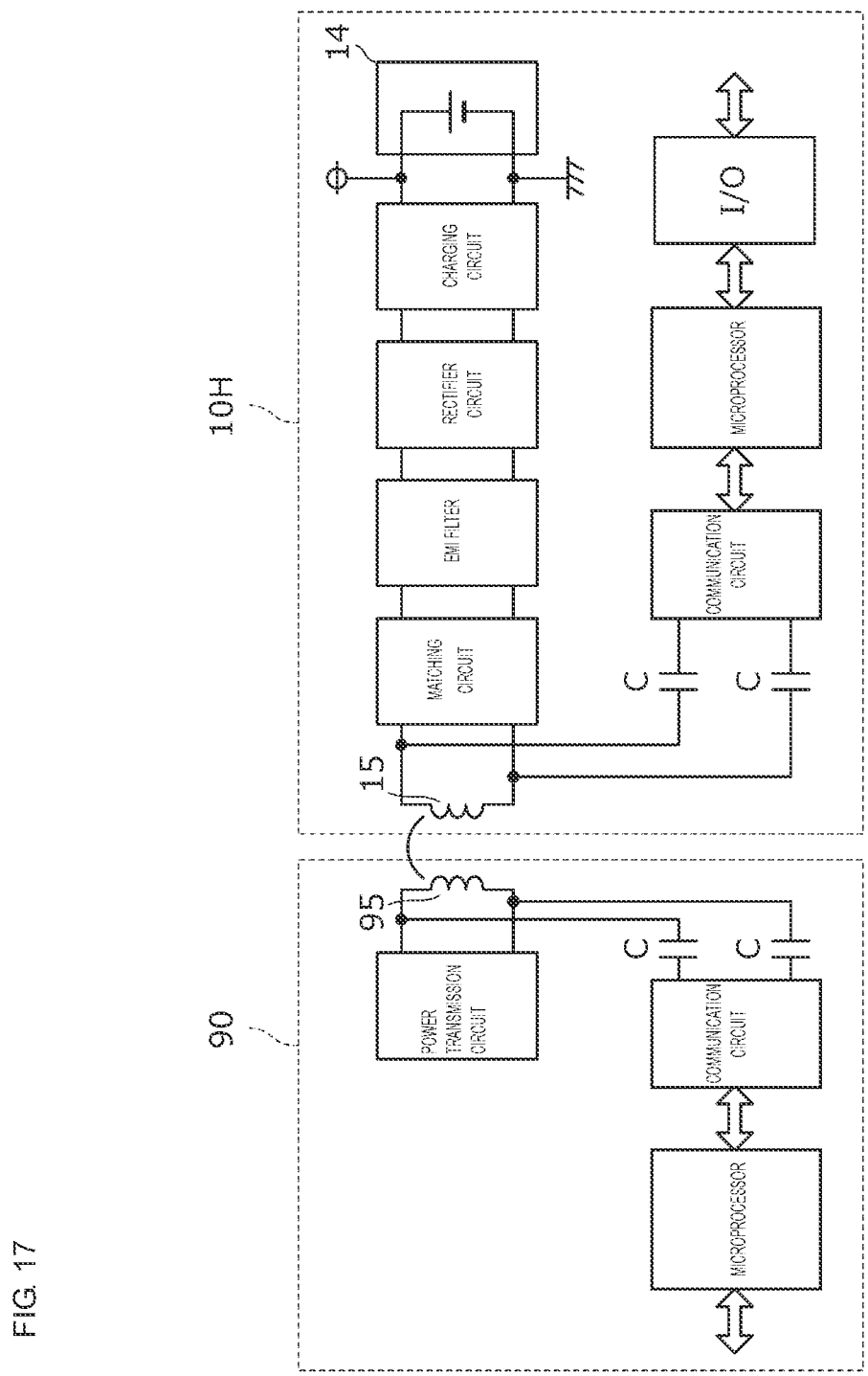
FIG. 17 is a block diagram illustrating a circuit configuration of a power supply system constituted by the in-vivo implantable medical device and a power transmission device.

FIG. 17 is a block diagram illustrating a circuit configuration of a power supply system constituted by the in-vivo implantable medical device 10H and the power transmission device 90. The power transmission device 90 is provided with the power transmission coil 95, a power transmission circuit connected thereto, a communication circuit, a microprocessor, and the like. The in-vivo implantable medical device 10H is provided with the power reception coil 15, a matching circuit, an EMI filter, a rectifier circuit, a charging circuit, and the secondary battery 14. These circuits constitute a circuit of a power supply system. In addition, the in-vivo implantable medical device 10H is provided with a communication circuit, a microprocessor, and an I/O circuit. These circuits constitute circuits of a signal processing system and an arithmetic system. The above communication circuit is connected to the power reception coil 15 with a capacitor C interposed therebetween.

The above rectifier circuit rectifies a current/voltage induced in the power reception coil, and the EMI filter removes an electromagnetic noise component. The rectifier circuit rectifies a received alternating current/voltage to a direct current. The charging circuit performs charge control of the secondary battery 14 with DC power outputted from the rectifier circuit.

The above I/O circuit inputs and outputs signals to and from various sensors connected thereto. The microprocessor performs predetermined signal processing and arithmetic processing. The communication circuit outputs data to external devices such as a power transmission device, other measurement devices, and a medical care device. This is performed by superimposing a signal in a predetermined format on a current flowing in the power reception coil 15.

Eighth Embodiment

In an eighth embodiment, an example of an in-vivo implantable medical device including a biological sensor outside a main body of the in-vivo implantable medical device will be illustrated.

Figure 18:
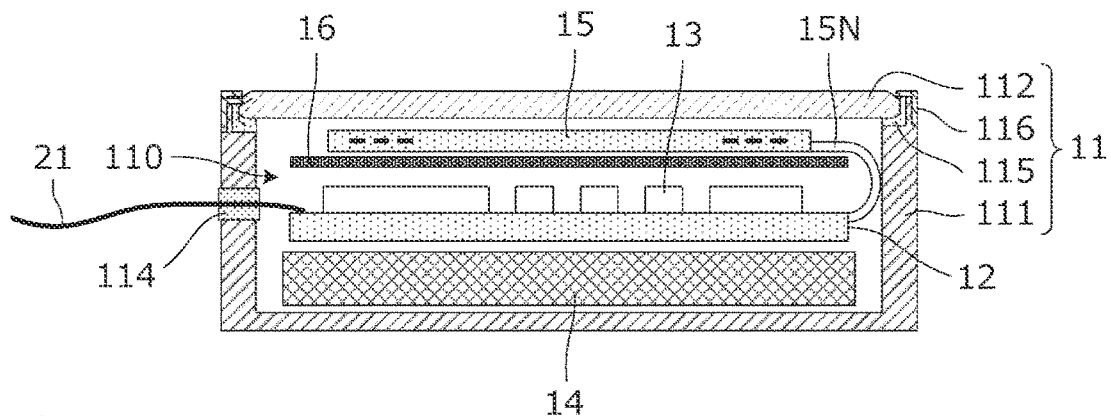
FIG. 18 is a sectional view of an in-vivo implantable medical device according to an eighth embodiment.
Figure 19:
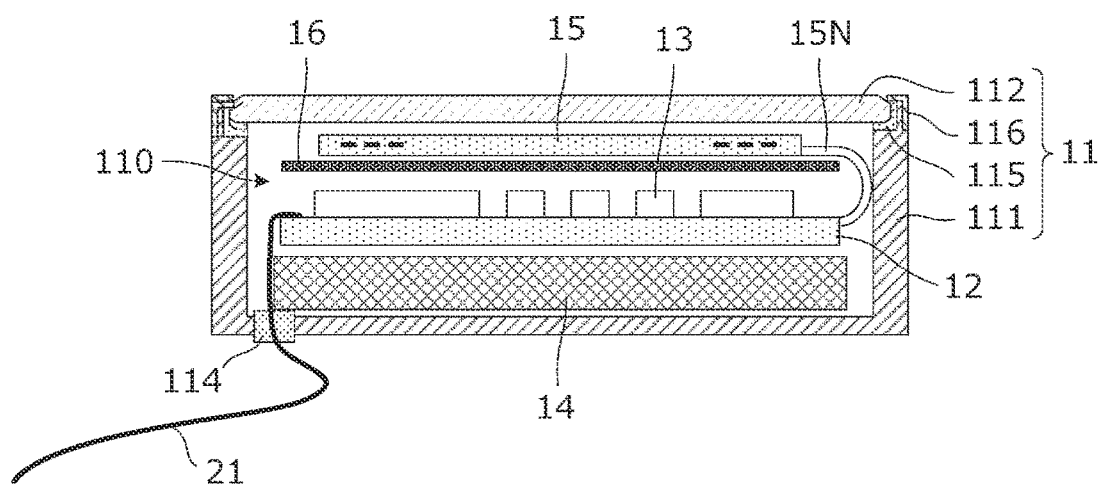
FIG. 19 is a sectional view of an in-vivo implantable medical device according to the eighth embodiment.
Figure 20:
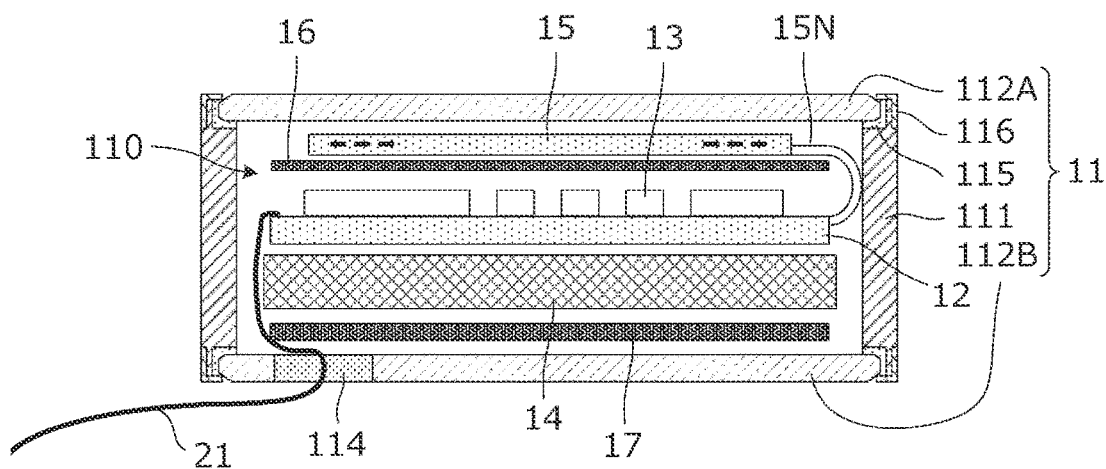
FIG. 20 is a sectional view of an in-vivo implantable medical device according to the eighth embodiment.

FIG. 18 is a sectional view of an in-vivo implantable medical device 10I according to the eighth embodiment, FIG. 19 is a sectional view of an in-vivo implantable medical device 10J according to the eighth embodiment, and FIG. 20 is a sectional view of an in-vivo implantable medical device 10K according to the eighth embodiment.

The in-vivo implantable medical device 10I illustrated in FIG. 18 is provided with the feedthrough 114 in a cylindrical sidewall portion of the first member 111 of the housing 11. The biological sensor 21 itself has a linear shape, and extends outside the housing 11 through the feedthrough 114.

The biological sensor 21 is connected to the circuit board 12 in the housing 11 through the feedthrough 114.

The feedthrough 114 is disposed at a position away from the power reception coil 15 in the housing 11. In the example illustrated in FIG. 18, the feed through 114 is disposed at a position where the magnetic material 16 is interposed between the feedthrough 114 and the power reception coil 15.

The in-vivo implantable medical device 10J illustrated in FIG. 19 is provided with the feedthrough 114 in a disk-shaped bottom plate portion of the first member 111 of the housing 11. Other configurations are similar to those in the in-vivo implantable medical device 10I illustrated in FIG. 18.

The in-vivo implantable medical device 10K illustrated in FIG. 20 includes the housing 11, the circuit board 12, the electronic circuit component 13, the secondary battery 14, the power reception coil 15, the magnetic material 16, and a magnetic material 17.

The housing 11 is constituted by the first member 111, second members 112A and 112B, the fixing ring 116, and the packing 115. The first member 111 has a cylindrical shape. The second members 112A and 112B each have a disk-like shape. The second members 112A and 112B are respectively fitted into two openings in the first member 111, with the packing 115 interposed therebetween. Further, the feedthrough 114 is provided in part of the second member 112B.

With such a configuration, the biological sensor 21 can be disposed outside the housing 11, and a degree of freedom in disposition of the biological sensor 21 is improved. Also, even when a main part of the feedthrough 114 is made of a metal material, the feedthrough 114 is disposed at a position magnetically separated from the power reception coil 15, and thus, magnetic coupling between the power reception coil 15 and the power transmission coil 95 (see, for example, FIG. 16) is not inhibited.

Note that, since a magnetic material 17 is disposed closer to an outside than the secondary battery 14 and the circuit board 12, even when strength of a magnetic field on a side of the second member 112B is high for some reason, an induced current flowing through the secondary battery 14 or a conductor pattern of and the circuit board 12 by the magnetic field from the outside is suppressed. Further, the magnetic material 17 constitutes part of a magnetic path suitable for forming magnetic coupling between the power reception coil 15 and the power transmission coil 95.

Ninth Embodiment

In a ninth embodiment, another example of structure of a fitting portion between a first member and a second member of a housing will be illustrated.

Figure 21A:
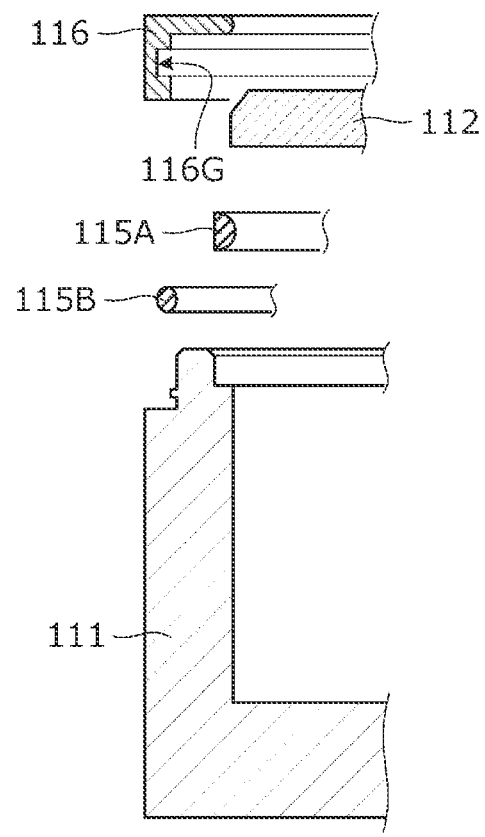
FIG. 21A and FIG. 21B are partial sectional views illustrating structure of a fitting portion of a second member and the like fit into an opening of the first member of the housing, in an in-vivo implantable medical device according to a ninth embodiment.
Figure 21B:
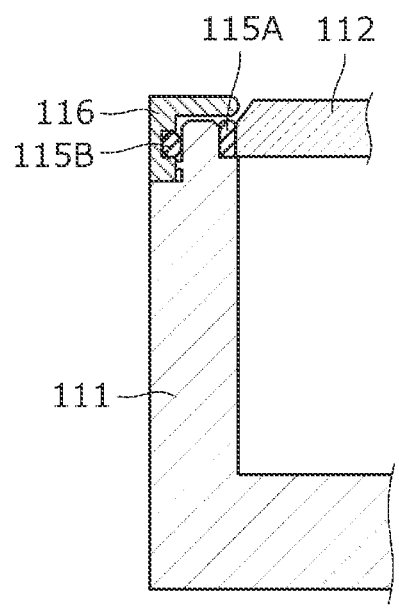

FIG. 21A and FIG. 21B are partial sectional views illustrating structure of a fitting portion of the second member 112 or the like fit into an opening of the first member 111 of the housing 11, in an in-vivo implantable medical device according to a ninth embodiment. FIG. 21A is the partial sectional view in a state before the first member 111 and the second member 112 of the housing 11, the fixing ring 116, and packings 115A and 115B are combined with each other.

FIG. 21B is the partial sectional view in a state in which those parts are combined with each other.

As illustrated in FIG. 21A, the fixing ring 116 in an annular shape is provided and holds the second member 112 in a direction in which the second member 112 is fitted into the opening of the first member 111. An outline of the fixing ring 116 is an annular shape, and a cross-section in a radial direction from a center of the annular shape is an L-shape. A groove 116G is formed in an inner peripheral edge of the fixing ring 116.

In the state illustrated in FIG. 21A, the packing 115B is attached to the groove 116G of the fixing ring 116, the packing 115A is attached to an inner peripheral edge of an opening of the first member 111, the second member 112 is placed thereon, and the fixing ring 116 is put thereon further from above, and the fixing ring 116 is screwed into an outer periphery of the opening of the first member 111. In this state, as illustrated in FIG. 21B, the packing 115B is sandwiched between the groove 116G of the fixing ring 116 and an outer peripheral edge of the opening of the first member 111. Further, the packing 115A is sandwiched between the inner peripheral edge of the opening of the first member 111 and an outer peripheral edge of the second member 112.

FIG. 22A, FIG. 22B, FIG. 22C, and FIG. 22D are views illustrating other shapes of packings sandwiched between a peripheral edge of the first member 111 and the second member 112 or sandwiched between the opening of the first member 111 and the fixing ring 116. Packings of various shapes can be used as a packing that is sandwiched between the peripheral edge of the opening of the first member 111 and the second member 112 or between the opening of the first member 111 and the fixing ring 116.

Figures 22A, 22B, 22C, 22D:
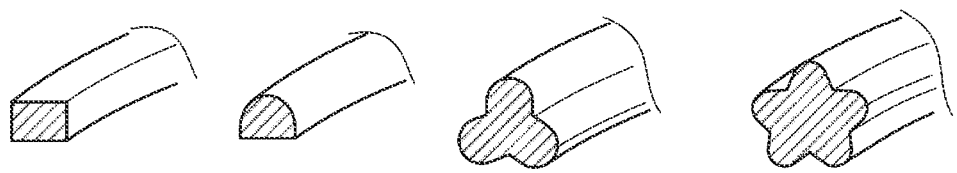
FIGS. 22A, 22B, 22C, and 22D are views illustrating other shapes of packings sandwiched between a peripheral edge of an opening of the first member and a second member, or sandwiched between the opening of the first member and a fixing ring.

As illustrated in FIG. 22A, a packing having a rectangular cross-section in a radial direction from a center of an annular shape may be used. The cross-section in the radial direction from the center of the annular shape may have a semicircular shape having a plane parallel to an annular circumferential surface. As illustrated in FIG. 22C and FIG. 22D, the cross-section in the radial direction from the center of the annular shape may have a flower-like shape having a plurality of petals.

Tenth Embodiment

A tenth embodiment illustrates an in-vivo implantable medical device that forms an electromagnetic resonance field between a power reception coil of the in-vivo implantable medical device and a power transmission coil that is external to a housing thereof and receives power from the power transmission coil.

Figure 23:
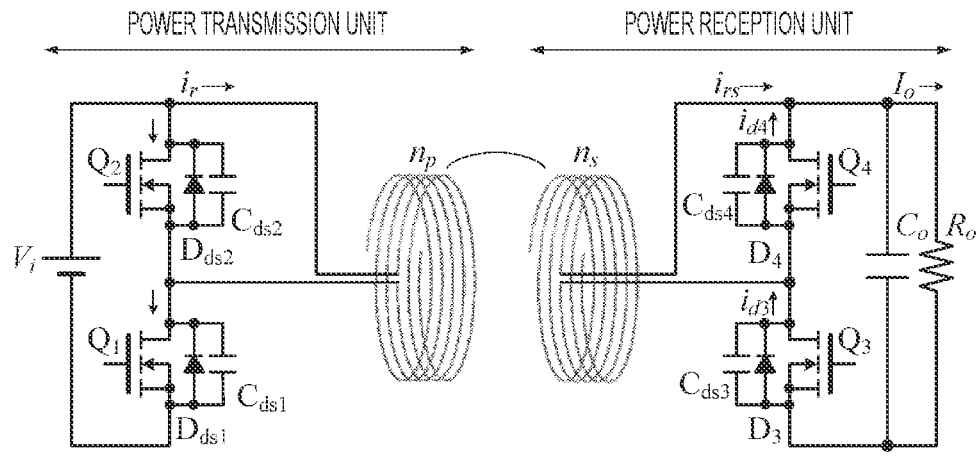
FIG. 23 is a circuit diagram of a power supply system, in an in-vivo implantable medical device according to a tenth embodiment, constituted by a power transmission unit of the power transmission device and a power reception unit of the in-vivo implantable medical device.
Figure 24:
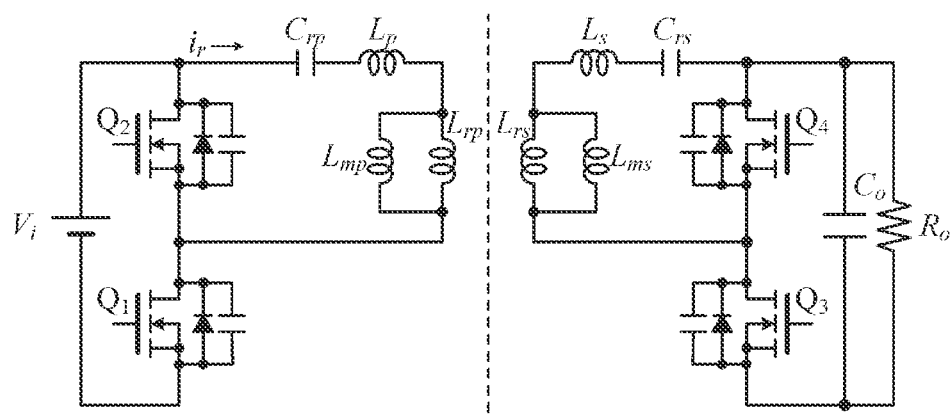
FIG. 24 is an equivalent circuit diagram of the power supply system illustrated in FIG. 23.
Figure 25:
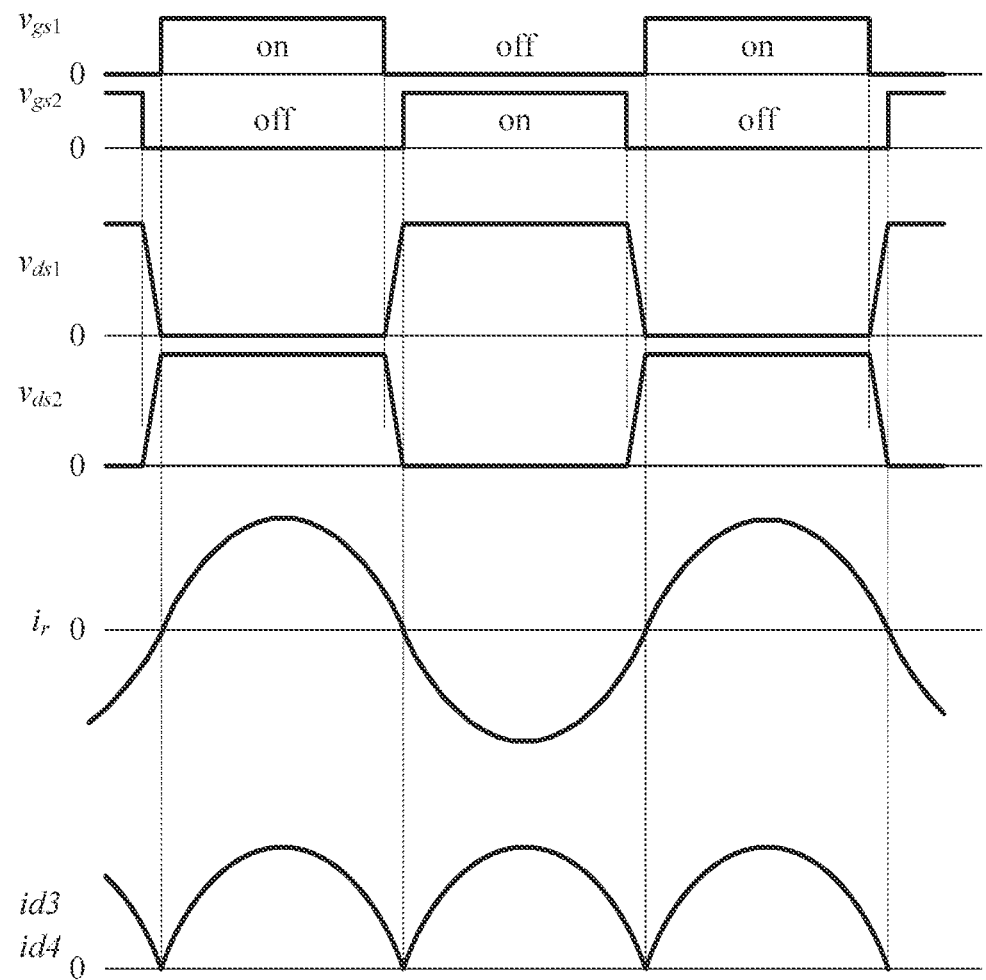
FIG. 25 is a waveform diagram of voltage/current in each section in FIG. 23 and FIG. 24.

FIG. 23 is a circuit diagram of a power supply system, in the in-vivo implantable medical device according to the tenth embodiment, constituted by a power transmission unit of the power transmission device 90 and a power reception unit of the in-vivo implantable medical device. FIG. 24 is an equivalent circuit diagram of the power supply system illustrated in FIG. 23. Further, FIG. 25 is a waveform diagram of voltage/current in each section in FIG. 23 and FIG. 24.

An input unit of the power transmission unit includes an input power supply Vi. The power transmission unit includes a power transmission coil np and an alternating current generation circuit electrically connected to the power transmission coil np. The power reception unit includes a power reception coil ns and a power reception circuit electrically connected to the power reception coil ns.

Each of the power transmission coil np and the power reception coil ns is a helical coil, and a center portion of each of the power transmission coil np and the power reception coil ns serves as an input/output portion. Thus, the power transmission coil np has equivalent inductances Lp, Lmp, and Lrp, and equivalent capacitance Crp, and these constitute a resonance circuit. Similarly, the power reception coil ns has inductances Ls, Lms, and Lrs, and capacitance Crs, and these constitute a resonance circuit. Respective winding axes of the two helical coils are substantially aligned (substantially coaxial) with each other, and thus, between the power transmission coil np and the power reception coil ns, electric field energy and magnetic field energy interact, thereby forming an electromagnetic resonance field.

A power transmission alternating current generating circuit includes a first switching circuit equivalently constituted by a parallel connection circuit of a first switching element Q1, a diode Dds1, and a capacitor Cds1 and a second switching circuit equivalently constituted by a parallel connection circuit of a second switching element Q2, a diode Dds2, and a capacitor Cds2.

The switching elements Q1 and Q2 are subjected to switching control by a switching control circuit (not illustrated). In FIG. 25, Vgs1 is a gate-source voltage signal of the first switching element Q1, and Vgs2 is a gate-source voltage signal of the second switching element Q2. As illustrated in FIG. 25, the first switching element Q1 and the second switching element Q2 are alternately turned on and off, thereby supplying an alternating voltage/alternating current to the power transmission coil np.

The above switching control circuit switches the first switching element Q1 and the second switching element Q2 at a predetermined operating frequency, thereby intermittently supplying a direct current voltage to the above resonance circuit, and generating a resonance current. This makes a voltage between both ends of the first switching circuit and the second switching circuit have a sinusoidal waveform of half-wave for each half cycle. For example, the switching operation is performed in 6.78 MHz or 13.56 MHz, which is an International ISM (Industrial, Scientific and Medical) band.

The power reception unit includes a power reception rectification circuit by switching elements Q3 and Q4 for rectifying an alternating current generated in the power reception coil ns, and a smoothing capacitor Co.

The switching elements Q3 and Q4 are controlled by a switching control circuit (not illustrated), and rectification is performed in synchronization with changes in a direction of a resonance current flowing through the power reception coil ns, and a direct current is supplied to a load Ro.

In a system in which wireless power supply is performed by electromagnetic field resonance coupling, unlike a system in which a high-frequency magnetic field is applied to a resonator, a process of the power supply can be simplified and a power loss can be reduced.

Finally, the description of the embodiments described above is illustrative in all respects and is not restrictive. Those skilled in the art can appropriately make modifications and variations. The scope of the present disclosure is indicated by the appended claims rather than by the foregoing embodiments. Further, the scope of the present disclosure includes modifications from the embodiments within the scope of the claims.

What is claimed is:

1. An in-vivo implantable medical device, comprising:
    a housing including a biocompatible material, and configured to define an internal space sealed;
    a power reception coil disposed in the internal space and configured to interact with an electromagnetic field generated by an electric field or magnetic field at an outside and generate an electromagnetic resonance field to receive power;
    a power storage device disposed in the internal space and configured to store power received through the power reception coil;
    a circuit board disposed in the internal space and including a first main surface and a second main surface opposite the first main surface;
    an electronic circuit disposed in the internal space and configured to perform at least signal processing by using power received by the power reception coil or power stored in the power storage device, the electronic circuit including an electronic component mounted on the first main surface; and
    a magnetic material directly attached to the second main surface of the circuit board,
    wherein the circuit board extends along an entirety of the magnetic material,
    wherein at least part of a region of the housing in which the electromagnetic resonance field is generated includes a biocompatible nonmetal material, and
    the power reception coil is a planar coil directly attached to the magnetic material on the second main surface of the circuit board.

2. The in-vivo implantable medical device according to claim 1, wherein
    the magnetic material is disposed between the power reception coil and the circuit board.

3. The in-vivo implantable medical device according to claim 2, wherein
    the magnetic material is a planar magnetic sheet and overlaps the power reception coil in plan view of the circuit board.

4. The in-vivo implantable medical device according to claim 2, wherein
    in plan view of the circuit board, a region where the electronic component is disposed overlaps at least part of a region where the power reception coil is disposed.

5. The in-vivo implantable medical device according to claim 1, wherein
    a part of the housing other than the region in which the electromagnetic resonance field is generated is made of a biocompatible metal material.

6. The in-vivo implantable medical device according to claim 5, wherein
    the biocompatible metal material of the housing is a first member having a box-like shape and having an opening,
    the biocompatible nonmetal material of the housing is a second member having a shape that closes the opening, and
    a packing having an annular shape and disposed between the first member and the second member is provided.

7. The in-vivo implantable medical device according to claim 6, wherein
    the housing includes a fixing member in an annular shape including a biocompatible metal material that holds the second member in a direction in which the second member is fitted into the opening of the first member.

8. The in-vivo implantable medical device according to claim 7, wherein the first member and the fixing member respectively have grooves for screw-fitting at contact portions where the first member and the fixing member being in contact with each other.

9. The in-vivo implantable medical device according to claim 6, wherein
the packing is made of a biocompatible nonmetal material.

10. The in-vivo implantable medical device according to claim 6, wherein
the packing is made of a synthetic polymer compound having a main skeleton by a siloxane bond.

11. The in-vivo implantable medical device according to claim 6,
wherein a cross-section in a radial direction from a center of the annular shape of the packing is a substantially L-shape.

12. The in-vivo implantable medical device according to claim 6, wherein
a biocompatible oil is applied to the packing.

13. The in-vivo implantable medical device according to claim 6, wherein
the biocompatible metal material is a material containing Ti or a titanium alloy made of Ti-6A1-4V as a main component.

14. The in-vivo implantable medical device according to claim 13, wherein
the biocompatible metal material is a sintered material of a mixture of ceramic powder and powder of the titanium alloy.

15. The in-vivo implantable medical device according to claim 6, wherein
the biocompatible nonmetal material is sapphire, ruby, glass, or ceramic.

16. The in-vivo implantable medical device according to claim 6, wherein
the coil generates the electromagnetic resonance field between the coil and a power transmission coil outside the housing and receives power from the power transmission coil.

17. The in-vivo implantable medical device according to claim 6, wherein
the magnetic material is configured to define, on a surface side in the housing opposite to the outside, part of a magnetic path of magnetic flux interlinked with the coil.

18. The in-vivo implantable medical device according to claim 1, further comprising:
a built-in communication module disposed in the internal space, electrically connected to the electronic circuit, and configured to communicate with an external communication module; and
a communication antenna connected to the built-in communication module,
wherein at least part of a portion of the housing, that serves as a radiation region of a radio wave of the communication antenna includes a biocompatible nonmetal material.

19. The in-vivo implantable medical device according to claim 18, wherein
the biocompatible nonmetal material disposed in the region in which the electromagnetic resonance field is generated and the biocompatible nonmetal material disposed in the portion that serves as the radiation region of the radio wave of the communication antenna are separated from each other.

20. The in-vivo implantable medical device according to claim 1, wherein
the electronic circuit includes a wireless communication circuit, and
the wireless communication circuit is configured to perform communication using the power reception coil.

21. The in-vivo implantable medical device according to claim 1, further comprising:
a feedthrough in part of the housing,
wherein the electronic circuit is electrically connected to a biological sensor located outside the housing through the feedthrough.

22. The in-vivo implantable medical device according to claim 1, wherein the circuit board extends along an entirety of the power reception coil.

23. An in-vivo implantable medical device, comprising:
a housing including a biocompatible material, and configured to define an internal space sealed;
a power reception coil disposed in the internal space;
a circuit board disposed in the internal space and including a first main surface and a second main surface opposite the first main surface;
an electronic circuit disposed in the internal space and configured to perform signal processing with power received by the power reception coil, the electronic circuit including an electronic component mounted on the first main surface; and
a magnetic material directly attached to the second main surface of the circuit board,
wherein the circuit board extends along an entirety of the magnetic material,
wherein a region of the housing, in which the power reception coil faces an outside of the housing, includes a biocompatible nonmetal material, and
the power reception coil is a planar coil directly attached to the magnetic material on the second main surface of the circuit board.

24. The in-vivo implantable medical device according to claim 23, wherein
a region of the housing other than the region that includes the biocompatible nonmetal material includes a biocompatible metal material.

25. The in-vivo implantable medical device according to claim 23,
wherein the magnetic material is configured to constitute part of a magnetic path of magnetic flux interlinked with the power reception coil.

26. The in-vivo implantable medical device according to claim 25, wherein
the magnetic material is a magnetic sheet that has a planar shape,
the power reception coil is located at a position sandwiched between the magnetic material and the biocompatible nonmetal material, and
in plan view of the magnetic material, the magnetic sheet overlaps the power reception coil.

27. The in-vivo implantable medical device according to claim 26, wherein
the magnetic material is disposed between the power reception coil and the circuit board.

28. The in-vivo implantable medical device according to claim 23, further comprising:
a power storage device configured to store power received by the power reception coil,
wherein the power storage device is disposed at one end of the housing in a first direction, and the power reception coil is disposed at another end of the housing in the first direction.

29. An in-vivo implantable medical device, comprising:

a housing including a biocompatible material and configured to define an internal space sealed;

a power reception coil disposed in the internal space;

a circuit board disposed in the internal space and including a first main surface and a second main surface opposite the first main surface;

an electronic circuit disposed in the internal space and configured to perform signal processing with power received by the power reception coil, the electronic circuit including an electronic component mounted on the first main surface; and a magnetic material directly attached to the second main surface of the circuit board, wherein the circuit board extends along an entirety of the magnetic material, wherein the housing includes a portion made of a biocompatible nonmetal material in a power reception path of power by the power reception coil, a region of the housing other than a region including the biocompatible nonmetal material includes a biocompatible metal material, and the power reception coil is a planar coil directly attached to the magnetic material on the second main surface of the circuit board.

* * * * *